(12) United States Patent
Ceccarelli et al.

(10) Patent No.: US 9,440,962 B2
(45) Date of Patent: Sep. 13, 2016

(54) BENZISOXAZOLES

(71) Applicant: Hoffmann-La Roche Inc., Little Falls, NJ (US)

(72) Inventors: Simona M. Ceccarelli, Basel (CH); Ravi Jagasia, Lorrach (DE); Roland Jakob-Roetne, Inzlingen (DE); Juergen Wichmann, Steinen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/602,541

(22) Filed: Jan. 22, 2015

(65) Prior Publication Data

US 2015/0259334 A1    Sep. 17, 2015

Related U.S. Application Data

(63) Continuation of application No. PCT/EP2013/065452, filed on Jul. 23, 2013.

(30) Foreign Application Priority Data

Jul. 26, 2012    (EP) .................................... 12177968

(51) Int. Cl.

| | |
|---|---|
| *A61K 31/41* | (2006.01) |
| *C07D 413/14* | (2006.01) |
| *C07D 413/04* | (2006.01) |
| *C07D 231/12* | (2006.01) |
| *C07D 401/04* | (2006.01) |

(52) U.S. Cl.
CPC ........... *C07D 413/14* (2013.01); *C07D 231/12* (2013.01); *C07D 401/04* (2013.01); *C07D 413/04* (2013.01)

(58) Field of Classification Search
None
See application file for complete search history.

(56) References Cited

FOREIGN PATENT DOCUMENTS

| WO | 2004/072033 A2 | 8/2004 |
| WO | 2006/044509 A2 | 4/2006 |

OTHER PUBLICATIONS

Longo, F. et al., Curr. Alzheimer Res 2006, vol. 3, pp. 5-10.*
International Search Report issued in International Application No. PCT/EP2013/065452, dated Aug. 27, 2013, in 4 pages.
Longo et al., "Small Molecule Approaches for Promoting Neurogenesis" Current Alzheimer Research 3:5-10 ( 2006).
Pokhodylo et al., "Synthesis of 2,1-Benzisoxazoles by Nucleophilic Substitution of Hydrogen in Nitroarenes Activated by the Azole Ring" Synthesis 16:2741-2748 (2009).

* cited by examiner

*Primary Examiner* — Heidi Reese

(57) ABSTRACT

The present invention relates to compounds of general formula

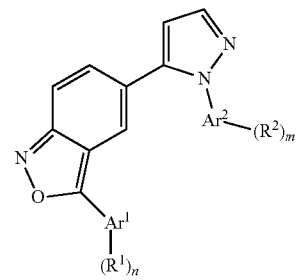

wherein
$Ar^1/Ar^2$ are phenyl or a 5 or 6-membered heteroaryl;
$R^1/R^2$ is hydrogen, halogen, lower alkyl, $CF_3$ or lower alkoxy;
n,m are 1 or 2;
or to a pharmaceutically acceptable acid addition salt, to a racemic mixture or to its corresponding enantiomer and/or optical isomers thereof, with the exception of the compound 2,1-benzisoxazole, 3-(4-chlorophenyl)-5-(1-phenyl-1H-pyrazol-5 -yl)-.
The compounds may be used for the treatment of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, abuse of neuro-active drugs, such as alcohol, opiates, methamphetamine, phencyclidine and cocaine.

9 Claims, No Drawings

BENZISOXAZOLES

CROSS REFERENCE TO RELATED APPLICATIONS

This application is a continuation of PCT/EP2013/065452 filed on Jul. 23, 2013, which is entitled to the priority of EP 12177968.0 filed on Jul. 26, 2012, the disclosures of which are incorporated herein by reference.

BACKGROUND OF THE INVENTION

Now it has been shown that the present compounds stimulate neurogenesis from neural stem cells (NSCs). Neurogenesis occurs in the developing and adult brain. Conceptually, this process of neurogenesis can be divided into four steps: (i) proliferation of NSCs; (ii) neuronal fate determination of NSC; (iii) survival and maturation of new neurons; and (iv) functional integration of new neurons into the neuronal network.

Adult neurogenesis is a developmental process that occurs throughout live in the adult brain whereby new functional neurons are generated from adult neural stem cells. Constitutive adult neurogenesis under physiological conditions occurs mainly in two "neurogenic" brain regions, 1) the sub-granular zone (SGZ) in the dentate gyrus of the hippocampus, where new dentate granule cells are generated, 2) the sub-ventricular zone (SVZ) of the lateral ventricles, where new neurons are generated and then migrate through the rostral migratory stream (RMS) to the olfactory bulb to become interneurons.

Extensive evidence suggests that hippocampal adult neurogenesis plays an important role in cognitive and emotional states albeit the precise function remains elusive. It has been argued that the relatively small number of newborn granule neurons can affect global brain function because they innervate many interneurons within the dentate gyrus, each of which inhibits hundreds of mature granule cells leading to a neurogenesis-dependent feedback inhibition. In combination with a low threshold for firing the newborn neurons trigger responses to very subtle changes in context. Disturbances in this process may manifest behaviorally in deficits in pattern separation related to psychiatric diseases. For example, adult hippocampal neurogenesis correlates with cognitive and emotional capacity, e.g. physical exercise, exposure to an enriched environment and typical antidepressants concomitantly promote adult hippocampal neurogenesis and cognition and/or emotional states, while chronic stress, depression, sleep deprivation and aging decrease adult neurogenesis and associate with negative cognitive and/or emotional states (Neuron 70, May 26, 2011, pp 582-588 and pp 687-702; WO 2008/046072).

Interestingly, antidepressants promote hippocampal adult neurogenesis and their effects on certain behaviors require the stimulation of neurogenesis. Neurogenesis in other adult CNS regions is generally believed to be very limited under normal physiological conditions, but could be induced after injury such as stroke, and central and peripheral brain damage.

It is therefore believed that stimulation of adult neurogenesis represents a neuro-regenerative therapeutic target for normal aging and in particular for a variety of neurodegenerative and neuropsychiatric diseases, including schizophrenia, obsessive-compulsive personality disorder, major depression, bipolar disorders, anxiety disorders, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss (Neuroscience, 167 (2010) 1216-1226; Nature Medicine, Vol. 11, number 3, (2005), 271-276) tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine (US 2012/0022096). Hence, chemical stimulation of adult neurogenesis offers new regenerative avenues and opportunities to develop novel drugs for treating neurological diseases and neuropsychiatric disorders.

SUMMARY OF THE INVENTION

The present invention relates to compounds of general formula

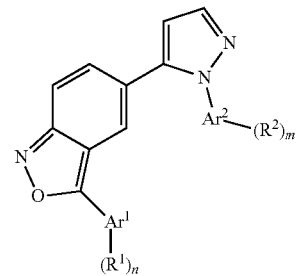

wherein
$Ar^1/Ar^2$ are phenyl or a 5- or 6-membered heteroaryl;
$R^1/R^2$ is hydrogen, halogen, lower alkyl, $CF_3$ or lower alkoxy;
n,m are 1 or 2;
or to a pharmaceutically acceptable acid addition salt, to a racemic mixture or to its corresponding enantiomer and/or optical isomers thereof, with the exception of the compound 2,1-benzisoxazole, 3-(4-chlorophenyl)-5-(1-phenyl-1H-pyrazol-5-yl)-. The excluded compound has been found in a public library.

The object of the present invention was to identify compounds that modulate neurogenesis. It has been found that the compounds of formula I are active in this area and they may therefore be used for the treatment of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine.

The most preferred indications for compounds of formula I are Alzheimer's disease, depression, anxiety disorders and stroke.

DETAILED DESCRIPTION OF THE INVENTION

The present invention relates to compounds of formula I and to their pharmaceutically acceptable salts, in cases where this applies to mixtures of enantiomers or diastereomers or their enantiomerically or diastereomerically pure forms, to these compounds as pharmaceutically active substances, to the processes for their production, as well as to the use in the treatment or prevention of disorders, relating to neurogenesis, schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, Parkinson's disease, dementia, Alzheimer's disease, mild cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, abuse of neuro-active drugs, such as alcohol, opiates, methamphetamine, phencyclidine and cocaine, and to pharmaceutical compositions containing the compounds of formula I.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-4 carbon atoms. Examples for "alkyl" are methyl, ethyl, n-propyl, and isopropyl.

The term "alkoxy" denotes a group —O—R' wherein R' is lower alkyl as defined above.

The term "5 or 6-membered heteroaryl" denotes a 5 or 6-membered aromatic ring, containing at least one N, O or S-heteroatom, for example pyridinyl, pyrimidinyl, pyrazolyl, pyridazinyl, imidazolyl, triazolyl, thiophenyl or pyraziny. A preferred 5- or 6-membered heteroaryl is pyridinyl or thiophenyl.

The term "halogen" denotes chlorine, bromine, fluorine or iodine.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention are compounds of formula

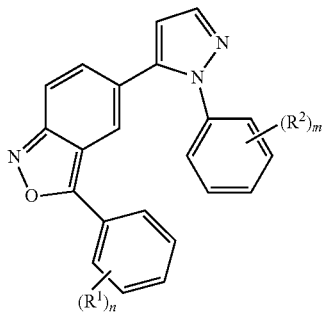

IA and
$R^1/R^2$ is hydrogen, halogen, lower alkyl, $CF_3$ or lower alkoxy;

n,m are 1 or 2;
or a pharmaceutically acceptable acid addition salt, a racemic mixture or its corresponding enantiomer and/or optical isomers thereof, with the exception of the compound 2,1-benzisoxazole, 3-(4-chlorophenyl)-5-(1-phenyl-1H-pyrazol-5-yl)-.

The following examples are encompassed by formula IA:
3-(4-Fluoro-phenyl)-5-[2-(2-fluoro-phenyl)-2H-pyrazol-3-yl]-benzo[c]isoxazole
3-(3-Fluoro-phenyl)-5-[2-(2-fluoro-phenyl)-2H-pyrazol-3-yl]-benzo[c]isoxazole
5-[2-(2-Fluoro-phenyl)-2H-pyrazol-3-yl]-3-p-tolyl-benzo[c]isoxazole
5-[2-(2-Fluoro-phenyl)-2H-pyrazol-3-yl]-3-(4-trifluoromethyl-phenyl)-benzo[c]isoxazole
3-(4-Chloro-phenyl)-5-[2-(2-fluoro-phenyl)-2H-pyrazol-3-yl]-benzo[c]isoxazole
5-[2-(2-Fluoro-phenyl)-2H-pyrazol-3-yl]-3-(4-methoxy-phenyl)-benzo[c]isoxazole
3-(4-Bromo-phenyl)-5-[2-(2-fluoro-phenyl)-2H-pyrazol-3-yl]benzo[c]isoxazole
3-(4-Fluoro-phenyl)-5-[2-(4-fluoro-phenyl)-2H-pyrazol-3-yl]-benzo[c]isoxazole
3-(4-Fluoro-phenyl)-5-[2-(3-fluoro-phenyl)-2H-pyrazol-3-yl]-benzo[c]isoxazole
3-(3-Fluoro-phenyl)-5-[2-(4-fluoro-phenyl)-2H-pyrazol-3-yl]-benzo[c]isoxazole
5-[2-(4-Fluoro-phenyl)-2H-pyrazol-3-yl]-3-p-tolyl-benzo[c]isoxazole
3-(4-Chloro-phenyl)-5-[2-(4-fluoro-phenyl)-2H-pyrazol-3-yl]-benzo[c]isoxazole
5-[2-(4-Fluoro-phenyl)-2H-pyrazol-3-yl]-3-(4-methoxy-phenyl)-benzo[c]isoxazole
3-(4-Fluoro-phenyl)-5-(2-p-tolyl-2H-pyrazol-3-yl)-benzo[c]isoxazole
3-(3-Fluoro-phenyl)-5-(2-p-tolyl-2H-pyrazol-3-yl)-benzo[c]isoxazole
3-p-Tolyl-5-(2-p-tolyl-2H-pyrazol-3-yl)-benzo[c]isoxazole
5-(2-p-Tolyl-2H-pyrazol-3-yl)-3-(4-trifluoromethyl-phenyl)-benzo[c]isoxazole
3-(4-Chloro-phenyl)-5-(2-p-tolyl-2H-pyrazol-3-yl)-benzo[c]isoxazole
3-(4-Methoxy-phenyl)-5-(2-p-tolyl-2H-pyrazol-3-yl)-benzo[c]isoxazole
3-(4-Fluoro-phenyl)-5-[2-(4-methoxy-phenyl)-2H-pyrazol-3-yl]-benzo[c]isoxazole
3-(3-Fluoro-phenyl)-5-[2-(4-methoxy-phenyl)-2H-pyrazol-3-yl]-benzo[c]isoxazole
5-[2-(4-Methoxy-phenyl)-2H-pyrazol-3-yl]-3-p-tolyl-benzo[c]isoxazole
3-(4-Chloro-phenyl)-5-[2-(4-methoxy-phenyl)-2H-pyrazol-3-yl]-benzo[c]isoxazole
3-(4-Methoxy-phenyl)-5-[2-(4-methoxy-phenyl)-2H-pyrazol-3-yl]-benzo[c]isoxazole
5-[2-(4-Chloro-phenyl)-2H-pyrazol-3-yl]-3-(4-fluoro-phenyl)-benzo[c]isoxazole
5-[2-(4-Chloro-phenyl)-2H-pyrazol-3-yl]-3-(3-fluoro-phenyl)-benzo[c]isoxazole
3-(4-Chloro-phenyl)-5-[2-(4-chloro-phenyl)-2H-pyrazol-3-yl]-benzo[c]isoxazole
5-[2-(2,4-Difluoro-phenyl)-2H-pyrazol-3-yl]-3-(4-fluoro-phenyl)-benzo[c]isoxazole
5-[2-(2,4-Difluoro-phenyl)-2H-pyrazol-3-yl]-3-(3-fluoro-phenyl)-benzo[c]isoxazole
5-[2-(2,4-Difluoro-phenyl)-2H-pyrazol-3-yl]-3-p-tolyl-benzo[c]isoxazole 5-[2-(2,4-Difluoro-phenyl)-2H-pyrazol-3-yl]-3-(4-trifluoromethyl-phenyl)-benzo[c]isoxazole 3-(4-Chloro-phenyl)-5-[2-(2,4-difluoro-phenyl)-2H-pyrazol-3-yl]-benzo[c]isoxazole 5-[2-(2,4-Difluoro-phenyl)-2H-pyrazol-3-yl]-3-(4-methoxy-phenyl)-benzo[c]isoxazole 3-Phenyl-5-(2-phenyl-2H-pyrazol-3-yl)-benzo[c]isoxazole 3-(3-Fluoro-4-methoxy-phenyl)-5-[2-(2-fluoro-phenyl)-2H-pyrazol-3-yl]-benzo[c]isoxazole 3-(3-Fluoro-4-methoxy-phenyl)-5-[2-(4-fluoro-phenyl)-2H-pyrazol-3-yl]-benzo[c]isoxazole 3-(3,4-Difluoro-phenyl)-5-(2-p-tolyl-2H-pyrazol-3-yl)-benzo[c]isoxazole 3-(3-Fluoro-4-methoxy-phenyl)-5-(2-p-tolyl-2H-pyrazol-3-yl)-benzo[c]isoxazole 5-[2-(2-Difluoro-phenyl)-2H-pyrazol-3-yl]-343-fluoro-4-methoxy-phenyl)-benzo[c]isoxazole 5-[2-(2-Chloro-phenyl)-2H-pyrazol-3-yl]-3-(4-fluoro-phenyl)-benzo[c]isoxazole 3-(4-Chloro-phenyl)-5-[2-(2-chloro-phenyl)-2H-pyrazol-3-yl]-benzo[c]isoxazole or 5-[2-(2-Chloro-phenyl)-2H-pyrazol-3-yl]-3-p-tolyl-benzo[c]isoxazole.

A further object of the present invention are compounds of formula

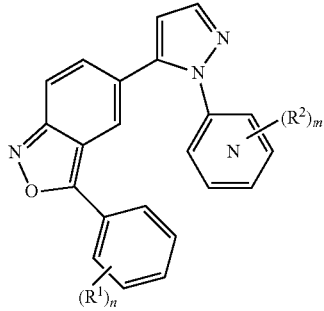

IB wherein

is a pyridine ring, wherein the N-atom may be in different positions, $R^1/R^2$ is hydrogen, halogen, lower alkyl, $CF_3$ or lower alkoxy; and n,m are 1 or 2;

or a pharmaceutically acceptable acid addition salt, a racemic mixture or its corresponding enantiomer and/or optical isomers thereof, for example the compound 3-(4-Fluoro-phenyl)-5-(2-pyridin-2-yl-2H-pyrazol-3-yl)-benzo[c]isoxazole A further object of the present invention are compounds of formula

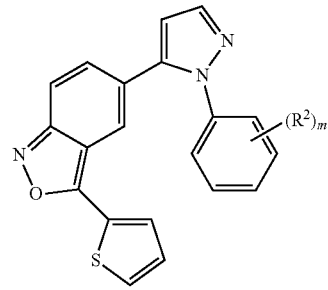

IC wherein $R^2$ is hydrogen, halogen, lower alkyl, $CF_3$ or lower alkoxy; and m is 1 or 2;

or a pharmaceutically acceptable acid addition salt, a racemic mixture or its corresponding enantiomer and/or optical isomers thereof, for example the following compound 5-[2-(4-Fluoro-phenyl)-2H-pyrazol-3-yl]-3-thiophen-2-yl-benzo[c]isoxazole The present compounds of formula I and their pharmaceutically acceptable salts can be prepared by methods known in the art, for example, by processes described below, which process comprises reacting a compound of formula

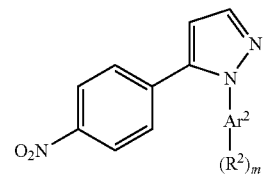

3 with a compound of formula

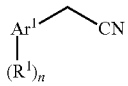

4 to a compound of formula

I wherein $Ar^1/Ar^2$ are phenyl or a 5 or 6-membered heteroaryl, $R^1/R^2$ is hydrogen, halogen, lower alkyl, $CF_3$ or lower alkoxy and n,m are 1 or 2;

and, if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

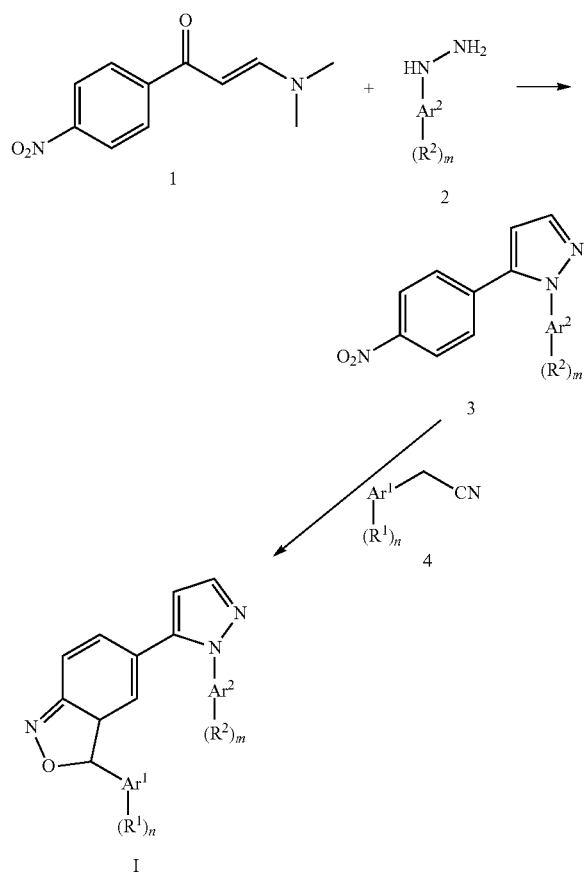

Scheme 1 wherein $Ar^1$, $Ar^e$, $R^1$, $R^2$ and n and m are as described above.

The compound of formula 1 (E)-3-dimethylamino-1-(4-nitrophenyl)-propenone is commercially available (CAS 78089-99-3).

The intermediate compound of formula 3 is prepared from a solution of commercially available (E)-3-(dimethylamino)-1-(4-nitrophenyl)-propenone [CAS No. 78089-99-3] 1 in acetic acid, and then phenylhydrazine 2 was added.

To a mixture of sodium hydroxide and MeOH is added a compound of formula 3 and a commercially available compound 4 to obtain the title compound of formula I.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have an activity as neurogenic agents.

The compounds were investigated in accordance with the test given hereinafter.

Neurogenesis Assay

Neural Stem Cell Proliferation Assay

Neurogenic properties of small molecules are determined based on the proliferation of human embryonic stem cell derived neural stem cells (NSCs) which were derived via a dual smad inhibition as previously described (Chambers, S. M., et al., *Highly efficient neural conversion of human ES and iPS cells by dual inhibition of SMAD signaling*, Nature biotechnology, 2009. 27(3): p. 275-80.)

Compounds respond is measured by the increase in cells based on ATP levels (Promega:CellTiterGlo®) after an incubation period of 4 days.

NSCs are thawed and expanded over 3 passages. On the 14$^{th}$ day, NSCs are seeded in Polyornithin/Laminin coated 384 well plates at a cell density of 21'000 cells/cm$^2$ in a media volume of 38 μl.

4 hours after cell seeding, compound solutions are added at a volume of 2 μl. Stock solutions of the compounds (water, 5% DMSO) are diluted to obtain a dose response (11 points, dilution factor is 2), ranging from 8 μM to 8 nM. Controls are run to consistently determine the neurogenic properties of the cells:

Negative (neutral) control is cell culture Media (final DMSO concentration: 0.25%).

Positive controls are:
1. cell culture Media+100 ng/ml FGF2 (final DMSO concentration: 0.1%)
2. cell culture Media+20 ng/ml EGF (final DMSO concentration: 0.1%)
3. cell culture Media+100 ng/ml Wnt3a (final DMSO concentration: 0.1%)

After 4 days incubation at 37° C., 5% CO$_2$, the amount of ATP per well is quantified. The ATP concentration is proportional to the cell number. ATP is quantified by using the Promega CellTiterGlo® kit. The CellTiterGlo® reagents contain a cell lysis buffer, a thermo stable luciferase (Ultra-Glo™ recombinant luciferase), magnesium and luciferin. Luciferin reacts with ATP producing oxyluciferin, AMP and light. The luminescence signal is proportional to the ATP content.

The value of negative (neutral) control is determined for each assay plate by taking the average of 16 negative control wells. The neurogenic compound response is calculated for each compound as (compound/Negative Control)* 100.

The values of EC$_{150}$ from the dose response curve are determined for each test compound. The EC150 is the compound concentration at which 150% activity of control (100%) is reached.

The preferred compounds show a EC $_{150}$ (μM) in the range of <2.8 μM as shown in the table below.

List of Examples and EC$_{150}$ Data

| Ex. | Structure | Name | EC$_{150}$ (uM) |
|---|---|---|---|
| 1 | | 3-(4-Fluoro-phenyl)-5-[2-(2-fluoro-phenyl)-2H-pyrazol-3-yl]-benzo[c]isoxazole | 0.12 |
| 2 | 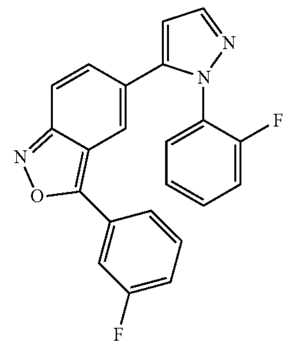 [SMILES: Fc1cccc(-c2onc3ccc(-c4ccnn4-c4ccccc4F)cc23)c1] | 3-(3-Fluoro-phenyl)-5-[2-(2-fluoro-phenyl)-2H-pyrazol-3-yl]-benzo[c]isoxazole | 0.29 |
| 3 | 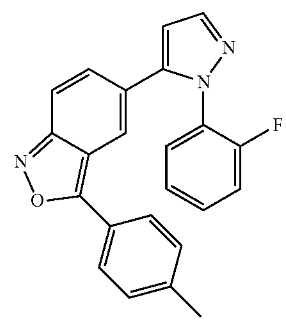 [SMILES: Cc1ccc(-c2onc3ccc(-c4ccnn4-c4ccccc4F)cc23)cc1] | 5-[2-(2-Fluoro-phenyl)-2H-pyrazol-3-yl]-3-p-tolyl-benzo[c]isoxazole | 0.12 |
| 4 | 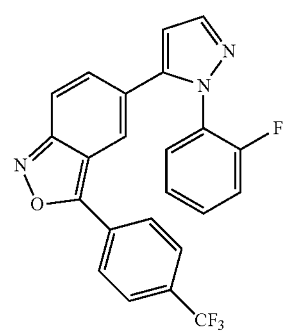 [SMILES: Fc1ccccc1-n1nccc1-c1ccc2noc(-c3ccc(C(F)(F)F)cc3)c2c1] | 5-[2-(2-Fluoro-phenyl)-2H-pyrazol-3-yl]-3-(4-trifluoromethyl-phenyl)-benzo[c]isoxazole | 0.92 |
| 5 | 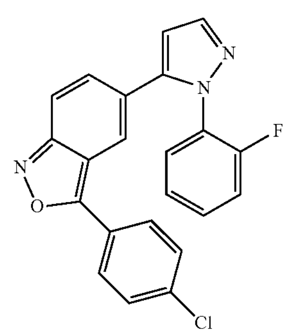 | 3-(4-Chloro-phenyl)-5-[2-(2-fluoro-phenyl)-2H-pyrazol-3-yl]-benzo[c]isoxazole | 0.033 |

| Ex. | Structure | Name | EC$_{150}$ (uM) |
|---|---|---|---|
| 6 | 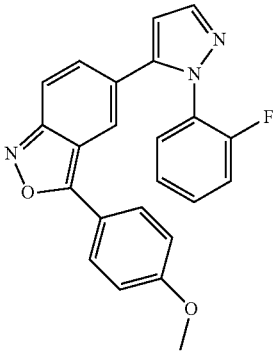 [SMILES: COc1ccc(-c2onc3ccc(-c4ccnn4-c4ccccc4F)cc23)cc1] | 5-[2-(2-Fluoro-phenyl)-2H-pyrazol-3-yl]-3-(4-methoxy-phenyl)-benzo[c]isoxazole | 0.073 |
| 7 | 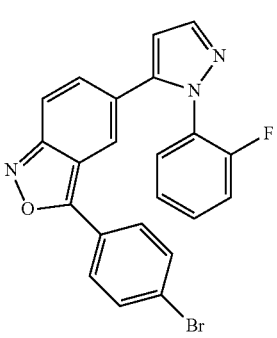 | 3-(4-Bromo-phenyl)-5-[2-(2-fluoro-phenyl)-2H-pyrazol-3-yl]benzo[c]isoxazole | 0.054 |
| 8 | 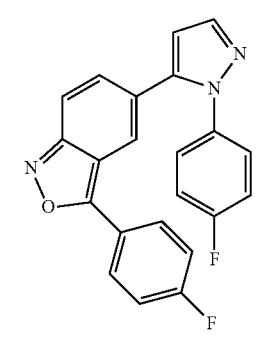 | 3-(4-Fluoro-phenyl)-5-[2-(4-fluoro-phenyl)-2H-pyrazol-3-yl]-benzo[c]isoxazole | 0.25 |
| 9 | 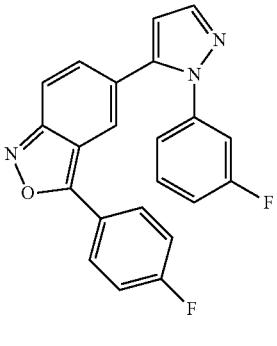 [SMILES: Fc1ccc(-c2onc3ccc(-c4ccnn4-c4cccc(F)c4)cc23)cc1] | 3-(4-Fluoro-phenyl)-5-[2-(3-fluoro-phenyl)-2H-pyrazol-3-yl]-benzo[c]isoxazole | 2.8 |
| 10 | 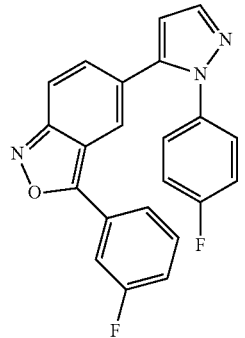 | 3-(3-Fluoro-phenyl)-5-[2-(4-fluoro-phenyl)-2H-pyrazol-3-yl]-benzo[c]isoxazole | 0.56 |
| 11 | 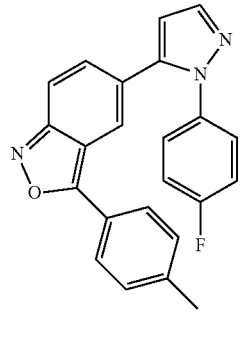 [SMILES: Cc1ccc(-c2onc3ccc(-c4ccnn4-c4ccc(F)cc4)cc23)cc1] | 5-[2-(4-Fluoro-phenyl)-2H-pyrazol-3-yl]-3-p-tolyl-benzo[c]isoxazole | 0.23 |
| 12 | 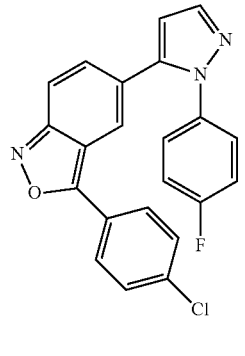 | 3-(4-Chloro-phenyl)-5-[2-(4-fluoro-phenyl)-2H-pyrazol-3-yl]-benzo[c]isoxazole | 0.26 |
| 13 | 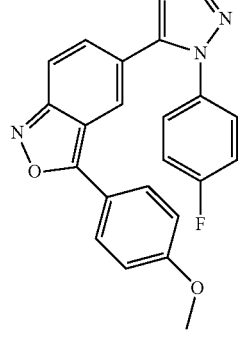 | 5-[2-(4-Fluoro-phenyl)-2H-pyrazol-3-yl]-3-(4-methoxy-phenyl)-benzo[c]isoxazole | 0.39 |

-continued

| Ex. | Structure | Name | EC$_{150}$ (uM) |
|---|---|---|---|
| 14 | 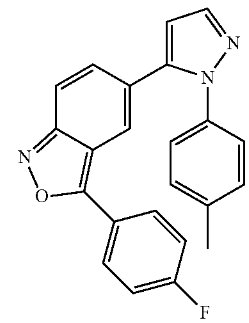 [SMILES: Cc1ccc(-n2nccc2-c2ccc3noc(-c4ccc(F)cc4)c3c2)cc1] | 3-(4-Fluoro-phenyl)-5-(2-p-tolyl-2H-pyrazol-3-yl)-benzo[c]isoxazole | 0.091 |
| 15 | 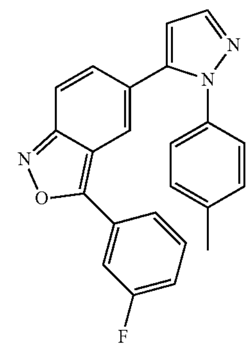 [SMILES: Cc1ccc(-n2nccc2-c2ccc3noc(-c4cccc(F)c4)c3c2)cc1] | 3-(3-Fluoro-phenyl)-5-(2-p-tolyl-2H-pyrazol-3-yl)-benzo[c]isoxazole | 0.14 |
| 16 | 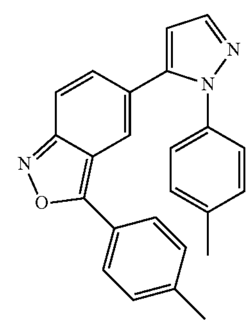 [SMILES: Cc1ccc(-c2onc3ccc(-c4ccnn4-c4ccc(C)cc4)cc23)cc1] | 3-p-Tolyl-5-(2-p-tolyl-2H-pyrazol-3-yl)-benzo[c]isoxazole | 0.055 |
| 17 | 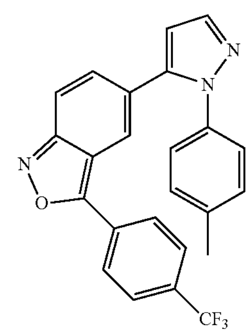 [SMILES: Cc1ccc(-n2nccc2-c2ccc3noc(-c4ccc(C(F)(F)F)cc4)c3c2)cc1] | 5-(2-p-Tolyl-2H-pyrazol-3-yl)-3-(4-trifluoromethyl-phenyl)-benzo[c]isoxazole | 1.13 |
| 18 | | 3-(4-Chloro-phenyl)-5-(2-p-tolyl-2H-pyrazol-3-yl)-benzo[c]isoxazole | 0.093 |
| 19 | | 3-(4-Methoxy-phenyl)-5-(2-p-tolyl-2H-pyrazol-3-yl)-benzo[c]isoxazole | 0.045 |
| 20 | | 3-(4-Fluoro-phenyl)-5-[2-(4-methoxy-phenyl)-2H-pyrazol-3-yl]-benzo[c]isoxazole | 0.36 |
| 21 | | 3-(3-Fluoro-phenyl)-5-[2-(4-methoxy-phenyl)-2H-pyrazol-3-yl]-benzo[c]isoxazole | 0.51 |

-continued

| Ex. | Structure | Name | EC$_{150}$ (uM) |
|---|---|---|---|
| 22 | 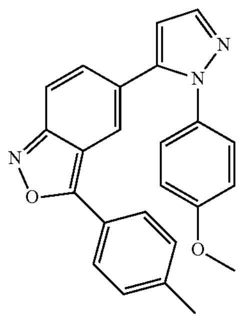 [SMILES: COc1ccc(-n2nccc2-c2ccc3noc(-c4ccc(C)cc4)c3c2)cc1] | 5-[2-(4-Methoxy-phenyl)-2H-pyrazol-3-yl]-3-p-tolyl-benzo[c]isoxazole | 0.18 |
| 23 | 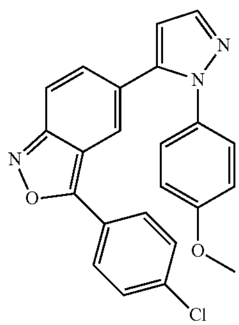 [SMILES: COc1ccc(-n2nccc2-c2ccc3noc(-c4ccc(Cl)cc4)c3c2)cc1] | 3-(4-Chloro-phenyl)-5-[2-(4-methoxy-phenyl)-2H-pyrazol-3-yl]-benzo[c]isoxazole | 0.31 |
| 24 | 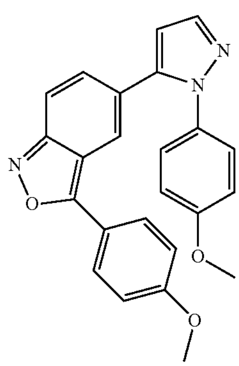 [SMILES: COc1ccc(-c2onc3ccc(-c4ccnn4-c4ccc(OC)cc4)cc23)cc1] | 3-(4-Methoxy-phenyl)-5-[2-(4-methoxy-phenyl)-2H-pyrazol-3-yl]-benzo[c]isoxazole | 0.26 |
| 25 | 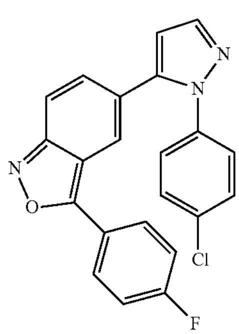 [SMILES: Fc1ccc(-c2onc3ccc(-c4ccnn4-c4ccc(Cl)cc4)cc23)cc1] | 5-[2-(4-Chloro-phenyl)-2H-pyrazol-3-yl]-3-(4-fluoro-phenyl)-benzo[c]isoxazole | 0.32 |

-continued

| Ex. | Structure | Name | EC$_{150}$ (uM) |
|---|---|---|---|
| 26 | | 5-[2-(4-Chloro-phenyl)-2H-pyrazol-3-yl]-3-(3-fluoro-phenyl)-benzo[c]isoxazole | 1.3 |
| 27 | | 3-(4-Chloro-phenyl)-5-[2-(4-chloro-phenyl)-2H-pyrazol-3-yl]-benzo[c]isoxazole | 0.46 |
| 28 | | 5-[2-(2,4-Difluoro-phenyl)-2H-pyrazol-3-yl]-3-(4-fluoro-phenyl)-benzo[c]isoxazole | 0.07 |
| 29 | | 5-[2-(2,4-Difluoro-phenyl)-2H-pyrazol-3-yl]-3-(3-fluoro-phenyl)-benzo[c]isoxazole | 0.25 |

| Ex. | Structure | Name | EC$_{150}$ (uM) |
|---|---|---|---|
| 30 | 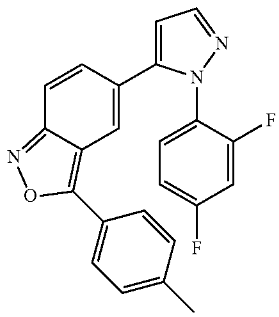 [SMILES: Cc1ccc(-c2onc3ccc(-c4ccnn4-c4ccc(F)cc4F)cc23)cc1] | 5-[2-(2,4-Difluoro-phenyl)-2H-pyrazol-3-yl]-3-p-tolyl-benzo[c]isoxazole | 0.04 |
| 31 | 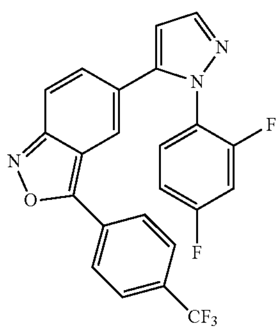 [SMILES: Fc1ccc(-n2nccc2-c2ccc3noc(-c4ccc(C(F)(F)F)cc4)c3c2)c(F)c1] | 5-[2-(2,4-Difluoro-phenyl)-2H-pyrazol-3-yl]-3-(4-trifluoromethyl-phenyl)-benzo[c]isoxazole | 0.96 |
| 32 | 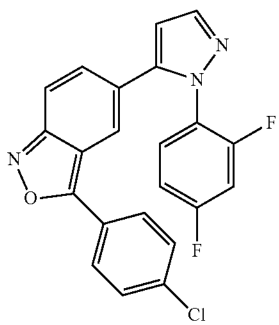 | 3-(4-Chloro-phenyl)-5-[2-(2,4-difluoro-phenyl)-2H-pyrazol-3-yl]-benzo[c]isoxazole | 0.073 |
| 33 | 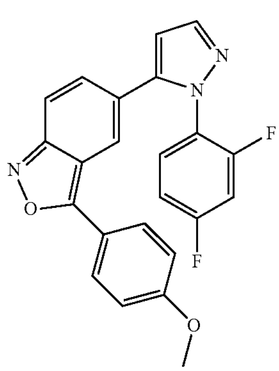 [SMILES: COc1ccc(-c2onc3ccc(-c4ccnn4-c4ccc(F)cc4F)cc23)cc1] | 5-[2-(2,4-Difluoro-phenyl)-2H-pyrazol-3-yl]-3-(4-methoxy-phenyl)-benzo[c]isoxazole | 0.068 |
| 34 | 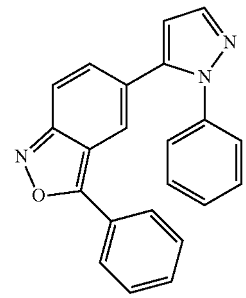 [SMILES: c1ccc(-c2onc3ccc(-c4ccnn4-c4ccccc4)cc23)cc1] | 3-Phenyl-5-(2-phenyl-2H-pyrazol-3-yl)-benzo[c]isoxazole | 0.13 |
| 35 | 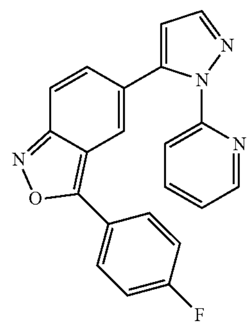 [SMILES: Fc1ccc(-c2onc3ccc(-c4ccnn4-c4ccccn4)cc23)cc1] | 3-(4-Fluoro-phenyl)-5-(2-pyridin-2-yl-2H-pyrazol-3-yl)-benzo[c]isoxazole | 0.04 |
| 36 | 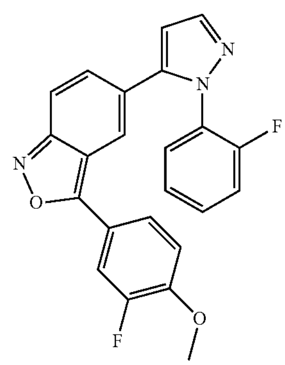 [SMILES: COc1ccc(-c2onc3ccc(-c4ccnn4-c4ccccc4F)cc23)cc1F] | 3-(3-Fluoro-4-methoxy-phenyl)-5-[2-(2-fluoro-phenyl)-2H-pyrazol-3-yl]-benzo[c]isoxazole | 0.16 |
| 37 | 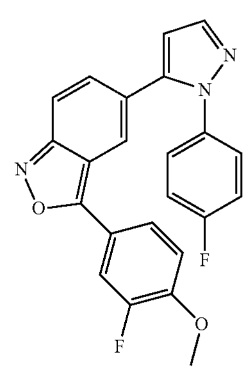 | 3-(3-Fluoro-4-methoxy-phenyl)-5-[2-(4-fluoro-phenyl)-2H-pyrazol-3-yl]-benzo[c]isoxazole | 1.1 |

-continued

| Ex. | Structure | Name | EC$_{150}$ (uM) |
|---|---|---|---|
| 38 | 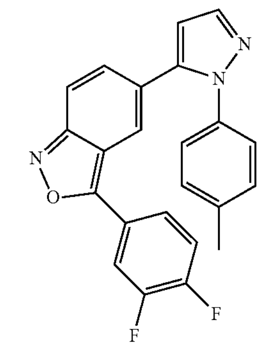 [SMILES: Cc1ccc(-n2nccc2-c2ccc3noc(-c4ccc(F)c(F)c4)c3c2)cc1] | 3-(3,4-Difluoro-phenyl)-5-(2-p-tolyl-2H-pyrazol-3-yl)-benzo[c]isoxazole | 0.48 |
| 39 | 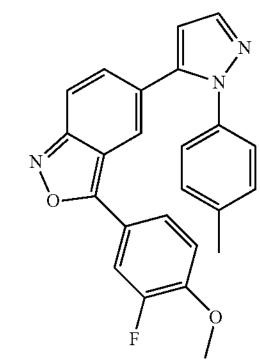 [SMILES: COc1ccc(-c2onc3ccc(-c4ccnn4-c4ccc(C)cc4)cc23)cc1F] | 3-(3-Fluoro-4-methoxy-phenyl)-5-(2-p-tolyl-2H-pyrazol-3-yl)-benzo[c]isoxazole | 0.25 |
| 40 | 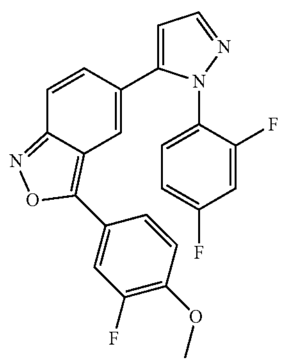 [SMILES: COc1ccc(-c2onc3ccc(-c4ccnn4-c4ccc(F)cc4F)cc23)cc1F] | 5-[2-(2,4-Difluoro-phenyl)-2H-pyrazol-3-yl]-3-(3-fluoro-4-methoxy-phenyl)-benzo[c]isoxazole | 0.23 |
| 41 | 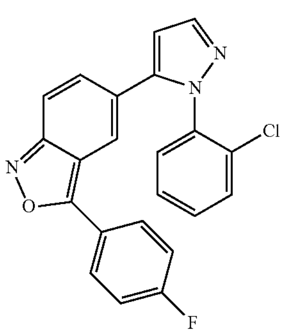 [SMILES: Fc1ccc(-c2onc3ccc(-c4ccnn4-c4ccccc4Cl)cc23)cc1] | 5-[2-(2-Chloro-phenyl)-2H-pyrazol-3-yl]-3-(4-fluoro-phenyl)-benzo[c]isoxazole | 0.22 |
| 42 | | 3-(4-Chloro-phenyl)-5-[2-(2-chloro-phenyl)-2H-pyrazol-3-yl]-benzo[c]isoxazole | 0.3 |
| 43 | | 5-[2-(2-Chloro-phenyl)-2H-pyrazol-3-yl]-3-p-tolyl-benzo[c]isoxazole | 0.15 |
| 44 | | 5-[2-(4-Fluoro-phenyl)-2H-pyrazol-3-yl]-3-thiophen-2-yl-benzo[c]isoxazole | 0.17 |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Pharmaceutical Compositions Comprising Compounds of the Invention

Tablet Formulation (Wet Granulation)

| Item | Ingredients | mg/tablet | | | |
|------|-------------|------|-------|--------|--------|
|      |             | 5 mg | 25 mg | 100 mg | 500 mg |
| 1.   | Compound of formula I | 5 | 25 | 100 | 500 |
| 2.   | Lactose Anhydrous DTG | 125 | 105 | 30 | 150 |
| 3.   | Sta-Rx 1500 | 6 | 6 | 6 | 30 |
| 4.   | Microcrystalline Cellulose | 30 | 30 | 30 | 150 |
| 5.   | Magnesium Stearate | 1 | 1 | 1 | 1 |
|      | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | mg/capsule | | | |
|------|-------------|------|-------|--------|--------|
|      |             | 5 mg | 25 mg | 100 mg | 500 mg |
| 1.   | Compound of formula I | 5 | 25 | 100 | 500 |
| 2.   | Hydrous Lactose | 159 | 123 | 148 | — |

-continued

Capsule Formulation

| Item | Ingredients | mg/capsule | | | |
|------|-------------|------|-------|--------|--------|
|      |             | 5 mg | 25 mg | 100 mg | 500 mg |
| 3.   | Corn Starch | 25 | 35 | 40 | 70 |
| 4.   | Talc | 10 | 15 | 10 | 25 |
| 5.   | Magnesium Stearate | 1 | 2 | 2 | 5 |
|      | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXPERIMENTAL PART

Intermediates

Intermediate A:
5-(4-Nitro-phenyl)-1-phenyl-1H-pyrazole

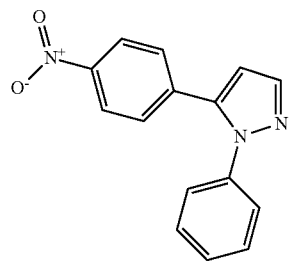 [SMILES: O=[N+]([O-])c1ccc(-c2ccnn2-c2ccccc2)cc1]

To a stirred solution of commercially available (E)-3-(dimethylamino)-1-(4-nitrophenyl)-propenone [CAS No. 78089-99-3] (100 mg, 454 μmol) in acetic acid (2 ml), phenylhydrazine (55.7 mg, 50.7 μl, 499 μmol) was added and the reaction mixture was allowed to stir for 2 h at room temperature, before it was heated under reflux conditions for 15 h. Afterwards the reaction mixture was evaporated, and further purified by flash chromatography on silica gel [Heptane/EtOAc (20-80%)] to yield the title compound as a yellow oil (115 mg, 96%), MS (ISP) m/z=266.3 [(M+H)$^+$].

Intermediate B: 1-(2-Fluoro-phenyl)-5-(4-nitro-phenyl)-1H-pyrazole

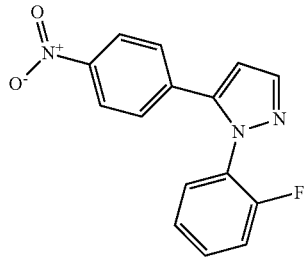 [SMILES: O=[N+]([O-])c1ccc(-c2ccnn2-c2ccccc2F)cc1]

The title compound, light brown oil (629 mg, 98%), MS (ISP) m/z=284.2 [(M+H)$^+$], was prepared in accordance with the general method of intermediate 1 from commercially available (E)-3-(dimethylamino)-1-(4-nitrophenyl)-propenone [CAS No. 78089-99-3] (0.5 g, 2.27 mmol) and (2-fluoro-phenyl)-hydrazine.

Intermediate C: 1-(4-Fluoro-phenyl)-5-(4-nitro-phenyl)-1H-pyrazole

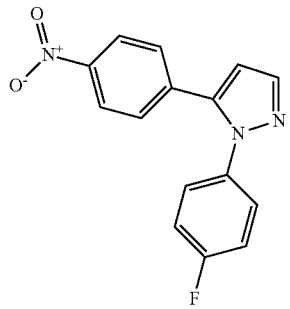 [SMILES: O=[N+]([O-])c1ccc(-c2ccnn2-c2ccc(F)cc2)cc1]

The title compound, light brown solid (1.29 g, 67%), MS (ISP) m/z=284.3 [(M+H)⁺], mp 135° C., was prepared in accordance with the general method of intermediate 1 from commercially available (E)-3-(dimethylamino)-1-(4-nitrophenyl)-propenone [CAS No. 78089-99-3] (1.5 mg, 6.81 mmol) and (4-fluoro-phenyl)-hydrazine.

Intermediate D: 1-(3-Fluoro-phenyl)-5-(4-nitro-phenyl)-1H-pyrazole

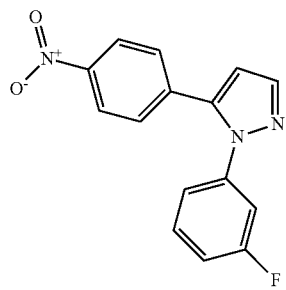 [SMILES: O=[N+]([O-])c1ccc(-c2ccnn2-c2cccc(F)c2)cc1]

The title compound, light brown solid (1.63 g, 85%), MS (ISP) m/z=284.3 [(M+H)⁺], mp 132° C., was prepared in accordance with the general method of intermediate 1 from commercially available (E)-3-(dimethylamino)-1-(4-nitrophenyl)-propenone [CAS No. 78089-99-3] (1.5 g, 6.81 mmol) and (3-fluoro-phenyl)-hydrazine.

Intermediate E:
5-(4-Nitro-phenyl)-1-p-tolyl-1H-pyrazole

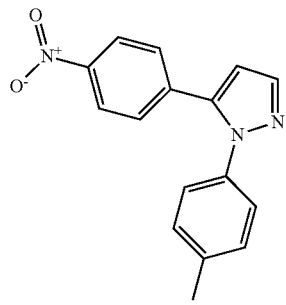 [SMILES: Cc1ccc(-n2nccc2-c2ccc([N+](=O)[O-])cc2)cc1]

The title compound, orange solid (1.37 g, 72%), MS (ISP) m/z=280.1 [(M+H)⁺], mp 121° C., was prepared in accordance with the general method of intermediate 1 from commercially available (E)-3-(dimethylamino)-1-(4-nitrophenyl)-propenone [CAS No. 78089-99-3] (1.5 g, 6.81 mmol) and (p-tolyl)-hydrazine.

Intermediate F: 5-(4-Nitro-phenyl)-1-(4-trifluoromethyl-phenyl)-1H-pyrazole

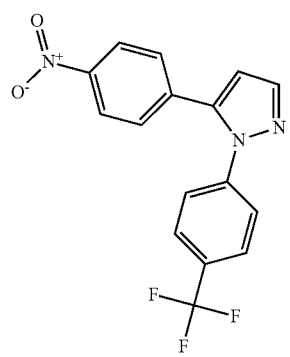 [SMILES: O=[N+]([O-])c1ccc(-c2ccnn2-c2ccc(C(F)(F)F)cc2)cc1]

The title compound, light brown solid (1.72 g, 76%), MS (ISP) m/z=334.2 [(M+H)⁺], mp 109° C., was prepared in accordance with the general method of intermediate 1 from commercially available (E)-3-(dimethylamino)-1-(4-nitrophenyl)-propenone [CAS No. 78089-99-3] (1.5 g, 6.81 mmol) and (4-trifluoromethyl-phenyl)-hydrazine.

Intermediate G: 1-(4-Methoxy-phenyl)-5-(4-nitro-phenyl)-1H-pyrazole

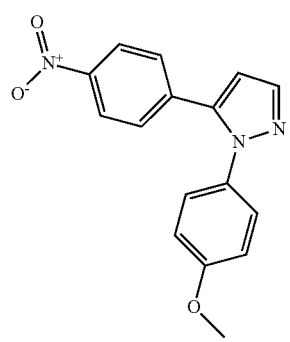 [SMILES: COc1ccc(-n2nccc2-c2ccc([N+](=O)[O-])cc2)cc1]

The title compound, light brown solid (1.73 g, 86%), MS (ISP) m/z=296.3 [(M+H)⁺], mp 137° C., was prepared in accordance with the general method of intermediate 1 from commercially available (E)-3-(dimethylamino)-1-(4-nitrophenyl)-propenone [CAS No. 78089-99-3] (1.5 g, 6.81 mmol) and (4-methoxy-phenyl)-hydrazine.

Intermediate H: 1-(4-Chloro-phenyl)-5-(4-nitro-phenyl)-1H-pyrazole

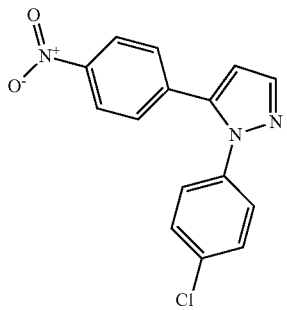 [SMILES: O=[N+]([O-])c1ccc(-c2ccnn2-c2ccc(Cl)cc2)cc1]

The title compound, light brown solid (1.17 g, 57%), MS (ISP) m/z=300.2 [(M+H)$^+$], mp 156° C., was prepared in accordance with the general method of intermediate 1 from commercially available (E)-3-(dimethylamino)-1-(4-nitrophenyl)-propenone [CAS No. 78089-99-3] (1.5 g, 6.81 mmol) and (4-chloro-phenyl)-hydrazine.

Intermediate I: 1-(2,4-Difluoro-phenyl)-5-(4-nitro-phenyl)-1H-pyrazole

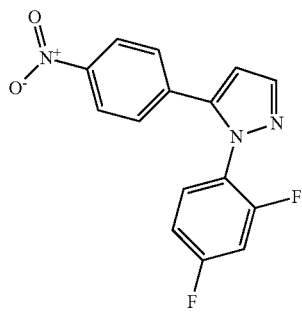 [SMILES: O=[N+]([O-])c1ccc(-c2ccnn2-c2ccc(F)cc2F)cc1]

The title compound, off-white solid (1.63 g, 79%), MS (ISP) m/z=300.2 [(M+H)$^+$], mp 113.5° C., was prepared in accordance with the general method of intermediate 1 from commercially available (E)-3-(dimethylamino)-1-(4-nitrophenyl)-propenone [CAS No. 78089-99-3] (1.5 g, 6.81 mmol) and (2,4-difluoro-phenyl)-hydrazine.

Intermediate K: 2-[5-(4-Nitro-nhenyl)-pyrazol-1-yl]pyridine

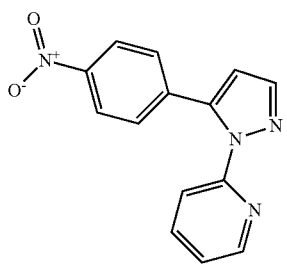 [SMILES: O=[N+]([O-])c1ccc(-c2ccnn2-c2ccccn2)cc1]

The title compound, brown oil (514 mg, 85%), MS (ISP) m/z=267.2 [(M+H)$^+$], was prepared in accordance with the general method of intermediate 1 from commercially available (E)-3-(dimethylamino)-1-(4-nitrophenyl)-propenone [CAS No. 78089-99-3] (0.5 g, 2.27 mmol) and 2-hydrazinyl-pyridine.

Intermediate L: 1-(2-Chloro-phenyl)-5-(4-nitro-phenyl)-1H-pyrazole

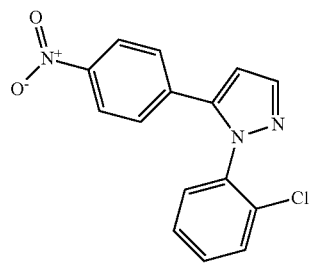 [SMILES: O=[N+]([O-])c1ccc(-c2ccnn2-c2ccccc2Cl)cc1]

The title compound, light brown solid (0.65 g, 96%), MS (ISP) m/z=300.2 [(M+H)$^+$], mp 130° C., was prepared in accordance with the general method of intermediate 1 from commercially available (E)-3-(dimethylamino)-1-(4-nitrophenyl)-propenone [CAS No. 78089-99-3] (0.5 g, 2.27 mmol) and (2-chloro-phenyl)-hydrazine.

Example 1

3-(4-Fluoro-phenyl)-5-[2-(2-fluoro-phenyl)-2H-pyrazol-3-yl]-benzo[c]isoxazole

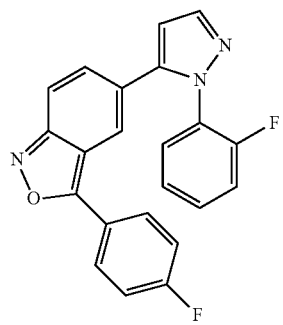

A mixture of sodium hydroxide (282 mg, 7.06 mmol) and MeOH (2.5 ml) was allowed to stir for 1 h at room temperature, 1-(2-fluoro-phenyl)-5-(4-nitro-phenyl)-1H-pyrazole (intermediate B) (200 mg, 706 μmol) and commercially available 2-(4-fluoro-phenyl)-acetonitrile (143 mg, 127 μl, 1.06 mmol) were added, and the reaction mixture was allowed to stir for 2 h at 60° C. The reaction mixture was poured into water (20 ml) and extracted with diethyl ether (2×40 ml). The combined organic layers were washed with brine (30 ml), dried (MgSO₄) and evaporated. The crude product was further purified by column chromatography on silica gel (toluene/ethyl acetate 95:5) followed by crystallization (ethyl acetate/heptane) to yield the title compound as a light yellow solid (184 mg, 70%), MS (ISP) m/z=374.1 [(M+H)⁺], mp 171° C.

Example 2

3-(3-Fluoro-phenyl)-5-[2-(2-fluoro-phenyl)-2H-pyrazol-3-yl]-benzo[c]isoxazole

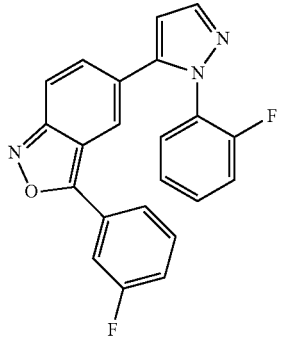 [SMILES: Fc1cccc(-c2onc3ccc(-c4ccnn4-c4ccccc4F)cc23)c1]

The title compound, light yellow solid (73 mg, 55%), MS (ISP) m/z=374.1 [(M+H)⁺], mp 186° C., was prepared in accordance with the general method of example 1 from 1-(2-fluoro-phenyl)-5-(4-nitro-phenyl)-1H-pyrazole (intermediate B) (100 mg, 353 μmol) and commercially available 2-(3-fluoro-phenyl)-acetonitrile.

Example 3

5-[2-(2-Fluoro-phenyl)-2H-pyrazol-3-yl]-3-p-tolyl-benzo[c]isoxazole

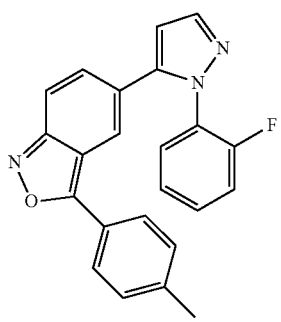 [SMILES: Cc1ccc(-c2onc3ccc(-c4ccnn4-c4ccccc4F)cc23)cc1]

The title compound, light green solid (92 mg, 71%), MS (ISP) m/z=370.1 [(M+H)⁻], mp 173° C., was prepared in accordance with the general method of example 1 from 1-(2-fluoro-phenyl)-5-(4-nitro-phenyl)-1H-pyrazole (intermediate B) (100 mg, 353 μmol) and commercially available 2-(p-tolyl)-acetonitrile.

Example 4

5-[2-(2-Fluoro-phenyl)-2H-pyrazol-3-yl]-3-(4-trifluoromethyl-phenyl)-benzo[c]isoxazole

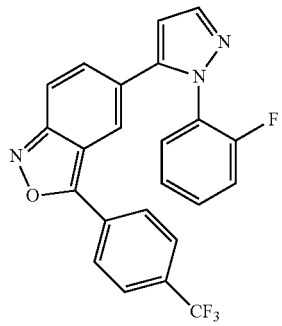 [SMILES: Fc1ccccc1-n1nccc1-c1ccc2noc(-c3ccc(C(F)(F)F)cc3)c2c1]

The title compound, light brown solid (88 mg, 59%), MS (ISP) m/z=424.2 [(M+H)⁺], mp 156° C., was prepared in accordance with the general method of example 1 from 1-(2-fluoro-phenyl)-5-(4-nitro-phenyl)-1H-pyrazole (intermediate B) (100 mg, 353 μmol) and commercially available 2-(4-trifluoromethyl-phenyl)-acetonitrile.

Example 5

3-(4-Chloro-phenyl)-5-[2-(2-fluoro-phenyl)-2H-pyrazol-3-yl]-benzo[c]isoxazole

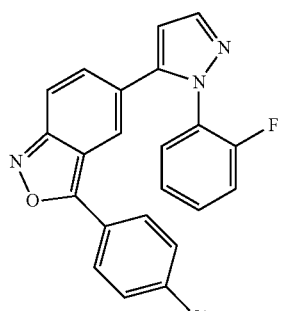

The title compound, light yellow solid (96 mg, 70%), MS (ISP) m/z=390.2 [(M+H)⁺], mp 191° C., was prepared in accordance with the general method of example 1 from 1-(2-fluoro-phenyl)-5-(4-nitro-phenyl)-1H-pyrazole (intermediate B) (100 mg, 353 μmol) and commercially available 2-(4-chloro-phenyl)-acetonitrile.

Example 6

5-[2-(2-Fluoro-phenyl)-2H-pyrazol-3-yl]-3-(4-methoxy-phenyl)-benzo[c]isoxazole

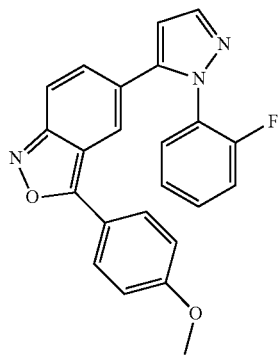

The title compound, light yellow solid (27 mg, 20%), MS (ISP) m/z=386.3 [(M+H)$^+$], mp 134° C., was prepared in accordance with the general method of example 1 from 1-(2-fluoro-phenyl)-5-(4-nitro-phenyl)-1H-pyrazole (intermediate B) (100 mg, 353 μmol) and commercially available 2-(4-methoxy-phenyl)-acetonitrile.

Example 7

3-(4-Bromo-phenyl)-5-[2-(2-fluoro-phenyl)-2H-pyrazol-3-yl]benzo[c]isoxazole

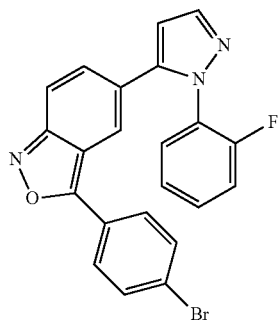 [SMILES: Fc1ccccc1-n1nccc1-c1ccc2noc(-c3ccc(Cl)cc3)c2c1]

The title compound, light yellow solid (108 mg, 71%), MS (ISP) m/z=434.2 [(M+H)$^+$], mp 202° C., was prepared in accordance with the general method of example 1 from 1-(2-fluoro-phenyl)-5-(4-nitro-phenyl)-1H-pyrazole (intermediate B) (100 mg, 353 μmol) and commercially available 2-(4-bromo-phenyl)-acetonitrile.

Example 8

3-(4-Fluoro-phenyl)-5-[2-(4-fluoro-phenyl)-2H-pyrazol-3-yl]-benzo[c]isoxazole

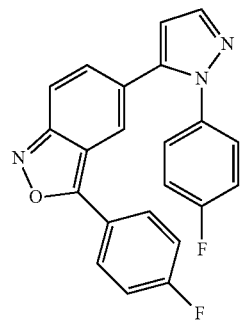 [SMILES: Fc1ccc(-c2onc3ccc(-c4ccnn4-c4ccc(F)cc4)cc23)cc1]

The title compound, light yellow solid (41 mg, 31%), MS (ISP) m/z=374.1 [(M+H)$^+$], mp 159° C., was prepared in accordance with the general method of example 1 from 1-(4-fluoro-phenyl)-5-(4-nitro-phenyl)-1H-pyrazole (intermediate C) (100 mg, 353 μmol) and commercially available 2-(4-fluoro-phenyl)-acetonitrile.

Example 9

3-(4-Fluoro-phenyl)-5-[2-(3-fluoro-phenyl)-2H-pyrazol-3-yl]-benzo[c]isoxazole

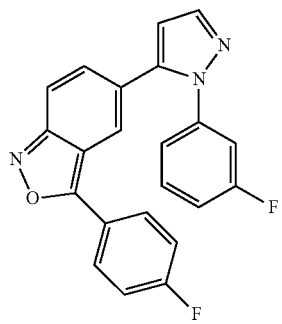 [SMILES: Fc1ccc(-c2onc3ccc(-c4ccnn4-c4cccc(F)c4)cc23)cc1]

The title compound, light grey solid (74 mg, 56%), MS (ISP) m/z=374.1 [(M+H)$^+$], mp 175° C., was prepared in accordance with the general method of example 1 from 1-(3-fluoro-phenyl)-5-(4-nitro-phenyl)-1H-pyrazole (intermediate D) (100 mg, 353 μmol) and commercially available 2-(4-fluoro-phenyl)-acetonitrile.

Example 10

3-(3-Fluoro-phenyl)-5-[2-(4-fluoro-phenyl)-2H-pyrazol-3-yl]-benzo[c]isoxazole

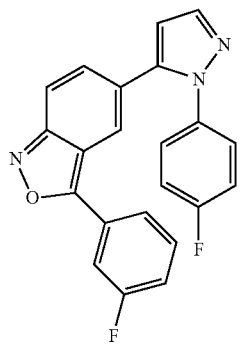

The title compound, light yellow solid (74 mg, 56%), MS (ISP) m/z=374.1 [(M+H)$^+$], mp 176° C., was prepared in accordance with the general method of example 1 from 1-(4-fluoro-phenyl)-5-(4-nitro-phenyl)-1H-pyrazole (intermediate C) (100 mg, 353 µmol) and commercially available 2-(3-fluoro-phenyl)-acetonitrile.

Example 11

5-[2-(4-Fluoro-phenyl)-2H--pyrazol-3-yl]-3-p-tolyl-benzo[c]isoxazole

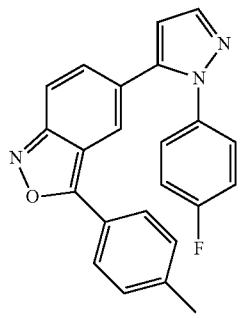

The title compound, yellow solid (28 mg, 22%), MS (ISP) m/z=370.2 [(M+H)$^+$], mp 158° C., was prepared in accordance with the general method of example 1 from 1-(4-fluoro-phenyl)-5-(4-nitro-phenyl)-1H-pyrazole (intermediate C) (100 mg, 353 µmol) and commercially available 2-(p-tolyl)-acetonitrile.

Example 12

3-(4-Chloro-phenyl)-5-[2-(4-fluoro-phenyl)-2H-pyrazol-3-yl]-benzo[c]isoxazole

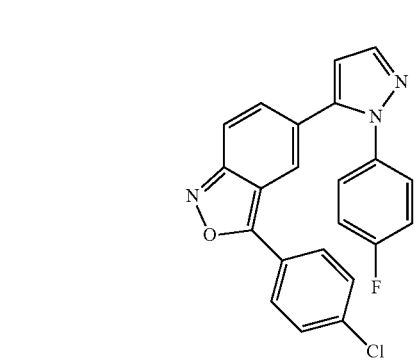 [SMILES: Fc1ccc(-n2nccc2-c2ccc3noc(-c4ccc(Cl)cc4)c3c2)cc1]

The title compound, yellow solid (81 mg, 59%), MS (ISP) m/z=390.2 [(M+H)$^+$], mp 188° C., was prepared in accordance with the general method of example 1 from 1-(4-fluoro-phenyl)-5-(4-nitro-phenyl)-1H-pyrazole (intermediate C) (100 mg, 353 µmol) and commercially available 2-(4-chloro-phenyl)-acetonitrile.

Example 13

5-[2-(4-Fluoro-phenyl)-2H-pyrazol-3-yl]-3-(4-methoxy-phenyl)-benzo[c]isoxazole

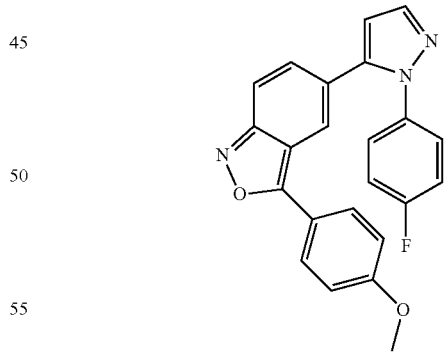

The title compound, yellow solid (35 mg, 26%), MS (ISP) m/z=386.3 [(M+H)$^+$], mp 153° C., was prepared in accordance with the general method of example 1 from 1-(4-fluoro-phenyl)-5-(4-nitro-phenyl)-1H-pyrazole (intermediate C) (100 mg, 353 µmol) and commercially available 2-(4-methoxy-phenyl)-acetonitrile.

Example 14

3-(4-Fluoro-phenyl)-5-(2-p-tolyl-2H-pyrazol-3-yl)-benzo[c]isoxazole

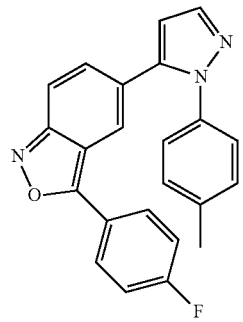

The title compound, light grey solid (50 mg, 38%), MS (ISP) m/z=370.2 [(M+H)$^+$], mp 173° C., was prepared in accordance with the general method of example 1 from 5-(4-nitro-phenyl)-1 p-tolyl-1H-pyrazole (intermediate E) (100 mg, 353 μmol) and commercially available 2-(4-fluoro-phenyl)-acetonitrile.

Example 15

3-(3-Fluoro-phenyl)-5-(2-p-tolyl-2H-pyrazol-3-yl)-benzo[c]isoxazole

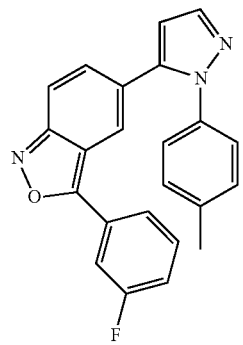

The title compound, light green solid (95 mg, 72%), MS (ISP) m/z=370.2 [(M+H)$^+$], mp 207° C., was prepared in accordance with the general method of example 1 from 5-(4-nitro-phenyl)-1-p-tolyl-1H-pyrazole (intermediate E) (100 mg, 353 μmol) and commercially available 2-(3-fluoro-phenyl)-acetonitrile.

Example 16

3-p-Tolyl-5-(2-p-tolyl-2H-pyrazol-3-yl)-benzo[c]isoxazole

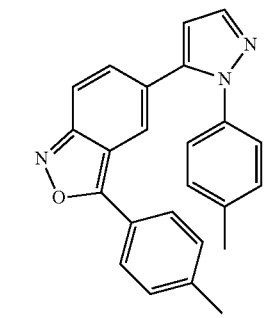

The title compound, yellow solid (35 mg, 27%), MS (ISP) m/z=366.2 [(M+H)$^+$], mp 190° C., was prepared in accordance with the general method of example 1 from 5-(4-nitro-phenyl)-1-p-tolyl-1H-pyrazole (intermediate E) (100 mg, 353 μmol) and commercially available 2-(p-tolyl)-acetonitrile.

Example 17

5-(2-p-Tolyl-2H-pyrazol-3-yl)-3-(4-trifluoromethyl-phenyl)-benzo[c]isoxazole

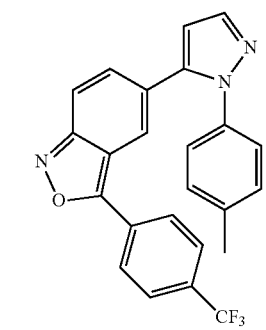

The title compound, yellow solid (41 mg, 27%), MS (ISP) m/z=420.2 [(M+H)$^+$], mp 173° C., was prepared in accordance with the general method of example 1 from 5-(4-nitro-phenyl)-1-p-tolyl-1H-pyrazole (intermediate E) (100 mg, 353 μmol) and commercially available 2-(4-trifluorom-ethyl-phenyl)-acetonitrile.

Example 18

3-(4-Chloro-phenyl)-5-(2-p-tolyl-2H-pyrazol-3-yl)-benzo[c]isoxazole

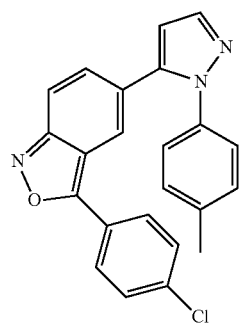

The title compound, light green solid (107 mg, 78%), MS (ISP) m/z=386.2 [(M+H)$^+$], mp 204° C., was prepared in accordance with the general method of example 1 from 5-(4-nitro-phenyl)-1-p-tolyl-1H-pyrazole (intermediate E) (100 mg, 353 μmol) and commercially available 2-(4-chloro-phenyl)-acetonitrile.

Example 19

3-(4-Methoxy-phenyl)-5-(2-p-tolyl-2H-pyrazol-3-yl)-benzo[c]isoxazole

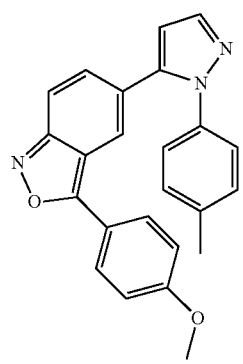

The title compound, light brown solid (17 mg, 12%), MS (ISP) m/z=382.4 [(M+H)$^+$], mp 165° C., was prepared in accordance with the general method of example 1 from 5-(4-nitro-phenyl)-1-p-tolyl-1H-pyrazole (intermediate E) (100 mg, 353 μmol) and commercially available 2-(4-methoxy-phenyl)-acetonitrile.

Example 20

3-(4-Fluoro-phenyl)-5-[2-(4-methoxy-phenyl)-2H-pyrazol-3-yl]-benzo[c]isoxazole

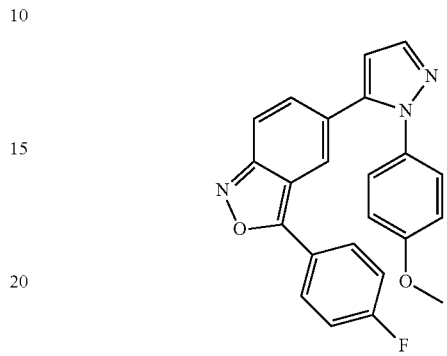

The title compound, light green solid (51 mg, 39%), MS (ISP) m/z=386.2 [(M+H)$^+$], mp 179° C., was prepared in accordance with the general method of example 1 from 1-(4-methoxy-phenyl)-5-(4-nitro-phenyl)-1H-pyrazole (intermediate G) (100 mg, 353 μmol) and commercially available 2-(4-fluoro-phenyl)-acetonitrile.

Example 21

3-(3-Fluoro-phenyl)-5-[2-(4-methoxy-phenyl)-2H-pyrazol-3-yl]-benzo[c]isoxazole

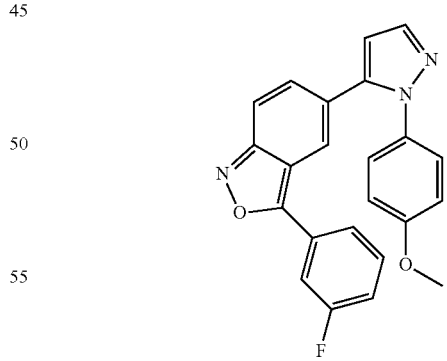

The title compound, light green solid (81 mg, 62%), MS (ISP) m/z=386.2 [(M+H)$^+$], mp 203° C., was prepared in accordance with the general method of example 1 from 1-(4-methoxy-phenyl)-5-(4-nitro-phenyl)-1H-pyrazole (intermediate G) (100 mg, 353 μmol) and commercially available 2-(3-fluoro-phenyl)-acetonitrile.

Example 22

5-[2-(4-Methoxy-phenyl)-2H-pyrazol-3-yl]-3-p-tolyl-benzo[c]isoxazole

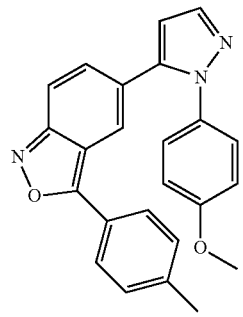

The title compound, light green solid (32 mg, 25%), MS (ISP) m/z=382.3 [(M+H)$^+$], mp 159° C., was prepared in accordance with the general method of example 1 from 1-(4-methoxy-phenyl)-5-(4-nitro-phenyl)-1H-pyrazole (intermediate G) (100 mg, 353 µmol) and commercially available 2-(p-tolyl)-acetonitrile.

Example 23

3-(4-Chloro-phenyl)-5-[2-(4-methoxy-phenyl)-2H-pyrazol-3-yl]-benzo[c]isoxazole

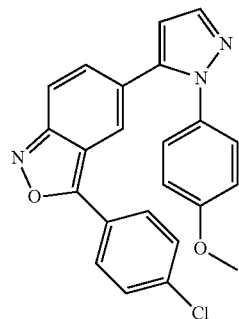

The title compound, light yellow solid (85 mg, 63%), MS (ISP) m/z=402.3 [(M+H)$^+$], mp 177° C., was prepared in accordance with the general method of example 1 from 1-(4-methoxy-phenyl)-5-(4-nitro-phenyl)-1H-pyrazole (intermediate G) (100 mg, 353 µmol) and commercially available 2-(4-chloro-phenyl)-acetonitrile.

Example 24

3-(4-Methoxy-phenyl)-5-[2-(4-methoxy-phenyl)-2H-pyrazol-3-yl]-benzo[c]isoxazole

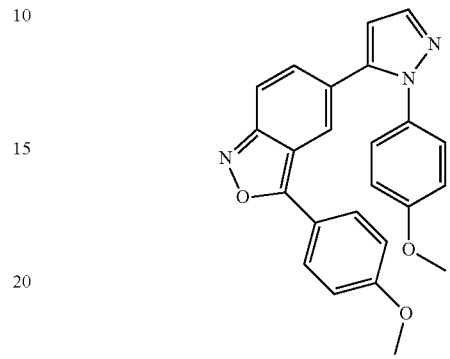

The title compound, yellow solid (7 mg, 5%), MS (ISP) m/z=398.2 [(M+H)$^+$], mp 133° C., was prepared in accordance with the general method of example 1 from 1-(4-methoxy-phenyl)-5-(4-nitro-phenyl)-1H-pyrazole (intermediate G) (100 mg, 353 µmol) and commercially available 2-(4-methoxy-phenyl)-acetonitrile.

Example 25

5-[2-(4-Chloro-phenyl)-2H-pyrazol-3-yl]-3-(4-fluoro-phenyl)-benzo[c]isoxazole

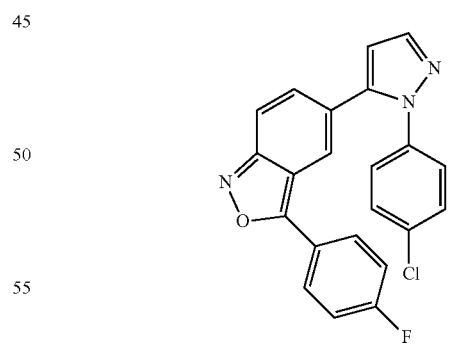

The title compound, yellow solid (28 mg, 22%), MS (ISP) m/z=390.2 [(M+H)$^+$], mp 154° C., was prepared in accordance with the general method of example 1 from 1-(4-chloro-phenyl)-5-(4-nitro-phenyl)-1H-pyrazole (intermediate H) (100 mg, 353 µmol) and commercially available 2-(4-fluoro-phenyl)-acetonitrile.

Example 26

5-[2-(4-Chloro-phenyl)-2H-pyrazol-3-yl]-3-(3-fluoro-phenyl)-benzo[c]isoxazole

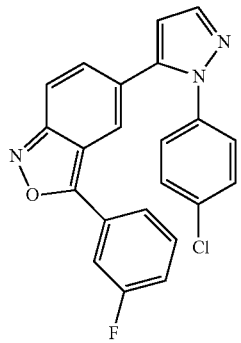

The title compound, light yellow solid (46 mg, 35%), MS (ISP) m/z=390.2 [(M+H)$^+$], mp 184° C., was prepared in accordance with the general method of example 1 from 1-(4-chloro-phenyl)-5-(4-nitro-phenyl)-1H-pyrazole (intermediate H) (100 mg, 353 μmol) and commercially available 2-(3-fluoro-phenyl)-acetonitrile.

Example 27

3-(4-Chloro-phenyl)-5-[2-(4-chloro-phenyl)-2H-pyrazol-3-yl]-benzo[c]isoxazole

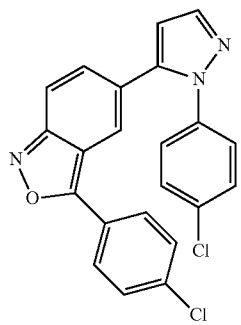

The title compound, light green solid (111 mg, 82%), MS (ISP) m/z=406.2 [(M+H)$^+$], mp 222° C., was prepared in accordance with the general method of example 1 from 1-(4-chloro-phenyl)-5-(4-nitro-phenyl)-1H-pyrazole (intermediate H) (100 mg, 353 μmol) and commercially available 2-(4-chloro-phenyl)-acetonitrile.

Example 28

5-[2-(2,4-Difluoro-phenyl)-2H-pyrazol-3-yl]-3-(4-fluoro-phenyl)-benzo[c]isoxazole

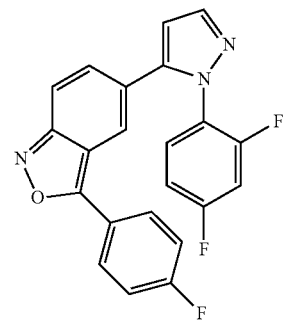

The title compound, light grey solid (22 mg, 17%), MS (ISP) m/z=392.2 [(M+H)$^+$], mp 149° C., was prepared in accordance with the general method of example 1 from 1-(2,4-difluoro-phenyl)-5-(4-nitro-phenyl)-1H-pyrazole (intermediate I) (100 mg, 353 μmol) and commercially available 2-(4-fluoro-phenyl)-acetonitrile.

Example 29

5-[2-(2,4-Difluoro-phenyl)-2H-pyrazol-3-yl]-3-(3-fluoro-phenyl)-benzo[c]isoxazole

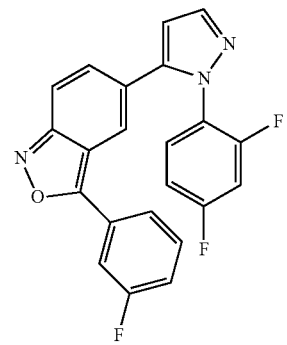 [SMILES: Fc1cccc(-c2onc3ccc(-c4ccnn4-c4ccc(F)cc4F)cc23)c1]

The title compound, light yellow solid (85 mg, 65%), MS (ISP) m/z=392.2 [(M+H)$^+$], mp 165° C., was prepared in accordance with the general method of example 1 from 1-(2,4-difluoro-phenyl)-5-(4-nitro-phenyl)-1H-pyrazole (intermediate I) (100 mg, 353 μmol) and commercially available 2-(3-fluoro-phenyl)-acetonitrile.

Example 30

5-[2-(2,4-Difluoro-phenyl)-2H-pyrazol-3-yl]-3-p-tolyl-benzo[c]isoxazole

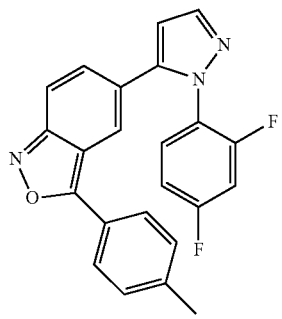 [SMILES: Cc1ccc(-c2onc3ccc(-c4ccnn4-c4ccc(F)cc4F)cc23)cc1]

The title compound, light yellow solid (13 mg, 10%), MS (ISP) m/z=388.2 [(M+H)⁺], mp 147° C., was prepared in accordance with the general method of example 1 from 1-(2,4-difluoro-phenyl)-5-(4-nitro-phenyl)-1H-pyrazole (intermediate I) (100 mg, 353 µmol) and commercially available 2-(p-tolyl)-acetonitrile.

Example 31

5-[2-(2,4-Difluoro-phenyl)-2H-pyrazol-3-yl]-3-(4-trifluoromethyl-phenyl)-benzo[c]isoxazole

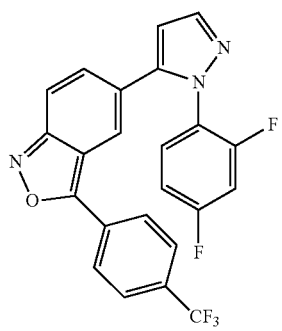

The title compound, light yellow solid (18 mg, 12%), MS (ISP) m/z=442.2 [(M+H)⁺], mp 159° C., was prepared in accordance with the general method of example 1 from 1-(2,4-difluoro-phenyl)-5-(4-nitro-phenyl)-1H-pyrazole (intermediate I) (100 mg, 353 µmol) and commercially available 2-(4-trifluoromethyl-phenyl)-acetonitrile.

Example 32

3-(4-Chloro-phenyl)-5-[2-(2,4-difluoro-phenyl)-2H-pyrazol-3-yl]-benzo[c]isoxazole

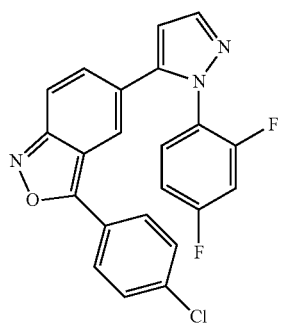 [SMILES: Fc1ccc(-n2nccc2-c2ccc3noc(-c4ccc(Cl)cc4)c3c2)c(F)c1]

The title compound, light green solid (71 mg, 53%), MS (ISP) m/z=408.2 [(M+H)⁺], mp 155° C., was prepared in accordance with the general method of example 1 from 1-(2,4-difluoro-phenyl)-5-(4-nitro-phenyl)-1H-pyrazole (intermediate I) (100 mg, 353 µmol) and commercially available 2-(4-chloro-phenyl)-acetonitrile.

Example 33

5-[2-(2,4-Difluoro-phenyl)-2H-pyrazol-3-yl]-3-(4-methoxy-phenyl)-benzo[c]isoxazole

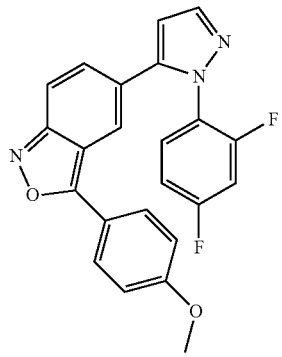 [SMILES: COc1ccc(-c2onc3ccc(-c4ccnn4-c4ccc(F)cc4F)cc23)cc1]

The title compound, yellow solid (21 mg, 16%), MS (ISP) m/z=404.3 [(M+H)⁺], mp 165° C., was prepared in accordance with the general method of example 1 from 1-(2,4-difluoro-phenyl)-5-(4-nitro-phenyl)-1H-pyrazole (intermediate I) (100 mg, 353 µmol) and commercially available 2-(4-methoxy-phenyl)-acetonitrile.

Example 34

3-Phenyl-5-(2-phenyl-2H-pyrazol-3-yl)-benzo[c]isoxazole

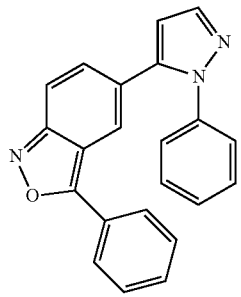

The title compound, light grey solid (37 mg, 29%), MS (ISP) m/z=338.3 [(M+H)+], mp 163° C., was prepared in accordance with the general method of example 1 from 5-(4-nitro-phenyl)-1-phenyl-1H-pyrazole (intermediate A) (100 mg, 353 µmol) and commercially available 2-phenyl-acetonitrile.

Example 35

3-(4-Fluoro-phenyl)-5-(2-pyridin-2-yl-2H-pyrazol-3-yl)-benzo[c]isoxazole

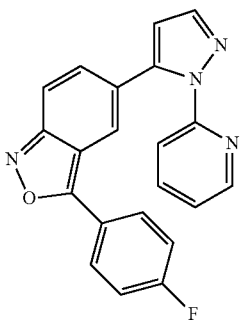 [SMILES: Fc1ccc(-c2onc3ccc(-c4ccnn4-c4ccccn4)cc23)cc1]

The title compound, light green solid (65 mg, 49%), MS (ISP) m/z=357.1 [(M+H)+], mp 175° C., was prepared in accordance with the general method of example 1 from 2-[5-(4-Nitro-phenyl)-pyrazol-1-yl]-pyridine (intermediate K) (100 mg, 353 µmol) and commercially available 2-(4-fluoro-phenyl)-acetonitrile.

Example 36

3-(3-Fluoro-4-methoxy-phenyl)-5-[2-(2-fluoro-phenyl)-2H-pyrazol-3-yl]-benzo[c]isoxazole

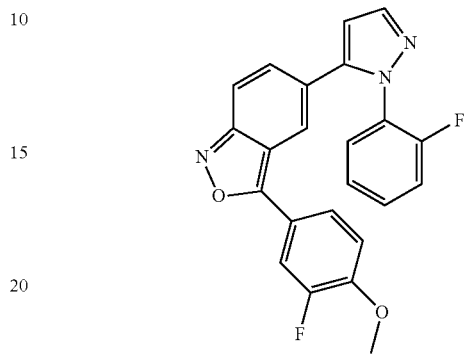

The title compound, yellow solid (55 mg, 39%), MS (ISP) m/z=404.3 [(M+H)+], mp 168° C., was prepared in accordance with the general method of example 1 from 1-(2-fluoro-phenyl)-5-(4-nitro-phenyl)-1H-pyrazole (intermediate B) (100 mg, 353 µmol) and commercially available 2-(3,4-difluoro-phenyl)-acetonitrile (exchange of one fluorine by methoxy during reaction).

Example 37

3-(3-Fluoro-4-methoxy-phenyl)-5-[2-(4-fluoro-phenyl)-2H-pyrazol-3-yl]-benzo[c]isoxazole

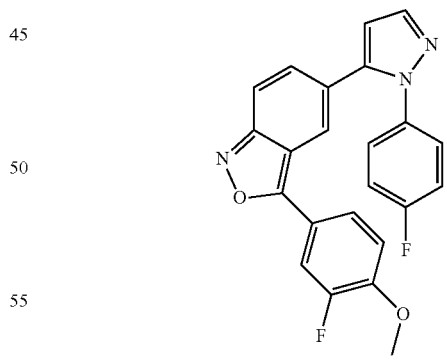

The title compound, yellow solid (58 mg, 41%), MS (ISP) m/z=404.4 [(M+H)+], mp 162° C., was prepared in accordance with the general method of example 1 from 1-(4-fluoro-phenyl)-5-(4-nitro-phenyl)-1H-pyrazole (intermediate C) (100 mg, 353 µmol) and commercially available 2-(3,4-difluoro-phenyl)-acetonitrile (exchange of one fluorine by methoxy during reaction).

Example 38

3-(3,4-Difluoro-phenyl)-5-(2-p-tolyl-2H-pyrazol-3-yl)-benzo[c]isoxazole

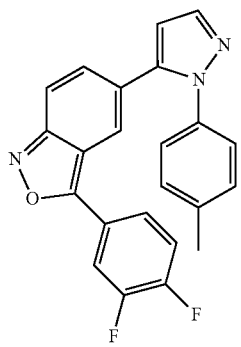

The title compound, light yellow solid (22 mg, 16%), MS (ISP) m/z=388.3 [(M+H)$^+$], mp 198° C., was prepared in accordance with the general method of example 1 from 5-(4-nitro-phenyl)-1-p-tolyl-1H-pyrazole (intermediate E) (100 mg, 353 µmol) and commercially available 2-(3,4-difluoro-phenyl)-acetonitrile (see also example 39).

Example 39

3-(3-Fluoro-4-methoxy-phenyl)-5-(2-p-tolyl-2H-pyrazol-3-yl)-benzo[c]isoxazole

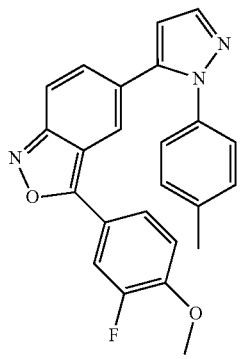

The title compound, yellow solid (57 mg, 40%), MS (ISP) m/z=400.3 [(M+H)$^+$], mp 197° C., was prepared in accordance with the general method of example 1 from 5-(4-nitro-phenyl)-1-p-tolyl-1H-pyrazole (intermediate E) (100 mg, 353 µmol) and commercially available 2-(3,4-difluoro-phenyl)-acetonitrile (partly exchange of one fluorine by methoxy during reaction, see also example 38).

Example 40

5-[2-(2,4-Difluoro-phenyl)-2H-pyrazol-3-yl]-3-(3-fluoro-4-methoxy-phenyl)-benzo[c]isoxazole

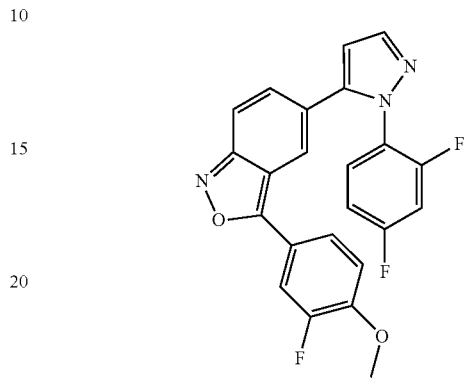

The title compound, yellow solid (64 mg, 46%), MS (ISP) m/z=422.3 [(M+H)$^+$], mp 183° C., was prepared in accordance with the general method of example 1 from 1-(2,4-difluoro-phenyl)-5-(4-nitro-phenyl)-1H-pyrazole (intermediate I) (100 mg, 353 µmol) and commercially available 2-(3,4-difluoro-phenyl)-acetonitrile (exchange of one fluorine by methoxy during reaction).

Example 41

5-[2-(2-Chloro-phenyl)-2H-pyrazol-3-yl]-3-(4-fluoro-phenyl)-benzo[c]isoxazole

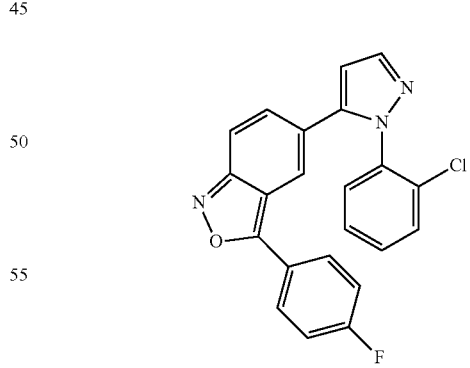

The title compound, green solid (53 mg, 41%), MS (ISP) m/z=390.2 [(M+H)$^+$], mp 161° C., was prepared in accordance with the general method of example 1 from 1-(2-chloro-phenyl)-5-(4-nitro-phenyl)-1H-pyrazole (intermediate L) (100 mg, 353 µmol) and commercially available 2-(4-fluoro-phenyl)-acetonitrile.

Example 42

3-(4-Chloro-phenyl)-5-[2-(2-chloro-phenyl)-2H-pyrazol-3-yl]-benzo[c]isoxazole

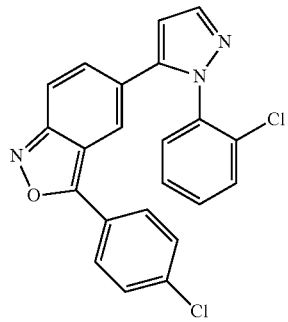 [SMILES: Clc1ccc(-c2onc3ccc(-c4ccnn4-c4ccccc4Cl)cc23)cc1]

The title compound, grey solid (110 mg, 81%), MS (ISP) m/z=406.2 [(M+H)$^+$], mp 172° C., was prepared in accordance with the general method of example 1 from 1-(2-chloro-phenyl)-5-(4-nitro-phenyl)-1H-pyrazole (intermediate L) (100 mg, 353 μmol) and commercially available 2-(4-chloro-phenyl)-acetonitrile.

Example 43

5-[2-(2-Chloro-phenyl)-2H-pyrazol-3-yl]-3-p-tolyl-benzo[c]isoxazole

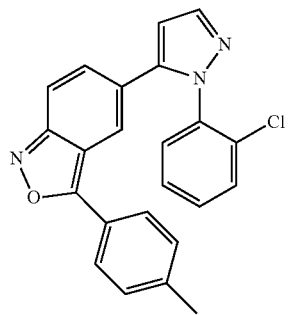 [SMILES: Cc1ccc(-c2onc3ccc(-c4ccnn4-c4ccccc4Cl)cc23)cc1]

The title compound, light green solid (39 mg, 30%), MS (ISP) m/z=386.2 [(M+H)$^+$], mp 176° C., was prepared in accordance with the general method of example 1 from 1-(2-chloro-phenyl)-5-(4-nitro-phenyl)-1H-pyrazole (intermediate L) (100 mg, 353 μmol) and commercially available 2-(p-tolyl)-acetonitrile.

Example 44

5-[2-(4-Fluoro-phenyl)-2H-1-pyrazol-3-yl]-3-thiophen-2-yl-benzo[c]isoxazole

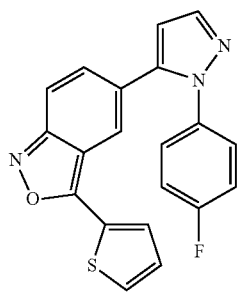 [SMILES: Fc1ccc(-n2nccc2-c2ccc3noc(-c4cccs4)c3c2)cc1]

The title compound, light brown solid (13 mg, 10%), MS (ISP) m/z=362.2 [(M+H)$^+$], mp 154° C., was prepared in accordance with the general method of example 1 from 1-(4-fluoro-phenyl)-5-(4-nitro-phenyl)-1H-pyrazole (intermediate C) (100 mg, 353 μmol) and commercially available 2-(thiophen-2-yl)-acetonitrile.

The invention claimed is:

1. A compound of formula

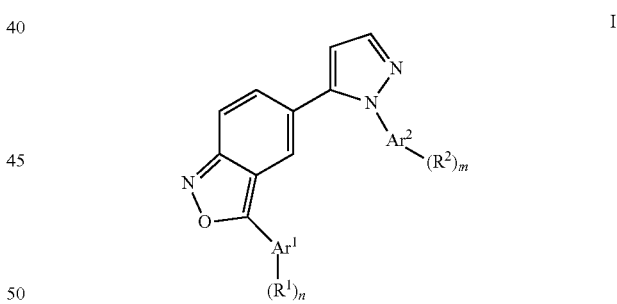

I wherein
   Ar$^1$/Ar$^2$ are phenyl or a 5 or 6-membered heteroaryl;
   R$^1$/R$^2$ is hydrogen, halogen, lower alkyl, CF$_3$ or lower alkoxy;
   n,m are 1 or 2;
   or a pharmaceutically acceptable acid addition salt, a racemic mixture or its corresponding enantiomer and/or optical isomers thereof, with the exception of the compound 2,1-benzisoxazole, 3-(4-chlorophenyl)-5-(1-phenyl-1H-pyrazol-5-yl).

2. A compound of formula IA encompassed by compounds of formula I according to claim 1

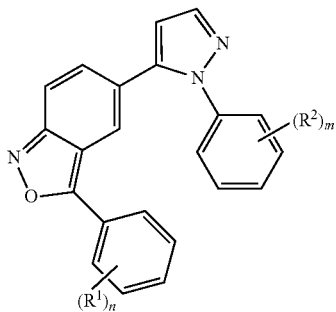

wherein
$R^1/R^2$ is hydrogen, halogen, lower alkyl, $CF_3$ or lower alkoxy;
n,m are 1 or 2;
or a pharmaceutically acceptable acid addition salt, a racemic mixture or its corresponding enantiomer and/or optical isomers thereof, with the exception of the compound 2,1-benzisoxazole, 3-(4-chlorophenyl)-5-(1-phenyl-1H-pyrazol-5-yl).

3. A compound of formula IA according to claim 1 wherein the compounds are:
   3-(4-Fluoro-phenyl)-5-[2-(2-fluoro-phenyl)-2H-pyrazol-3-yl]-benzo[c]isoxazole;
   3-(3-Fluoro-phenyl)-5-[2-(2-fluoro-phenyl)-2H-pyrazol-3-yl]-benzo[c]isoxazole;
   5-[2-(2-Fluoro-phenyl)-2H-pyrazol-3-yl]-3-p-tolyl-benzo[c]isoxazole;
   5-[2-(2-Fluoro-phenyl)-2H-pyrazol-3-yl]-3-(4-trifluoromethyl-phenyl)-benzo[c]isoxazol;
   3-(4-Chloro-phenyl)-5-[2-(2-fluoro-phenyl)-2H-pyrazol-3-yl]-benzo[c]isoxazole;
   5-[2(2-Fluoro-phenyl)-2H-pyrazol-3-yl]-3-(4-methoxy-phenyl)-benzo[c]isoxazole;
   3-(4-(4-Bromo-phenyl)-5-[2-(2-fluoro-phenyl)-2-H-pyrazol-3-yl]benzo[c]isoxazole;
   3-(4-Fluoro-phenyl)-5-[2-(4-fluoro-phenyl)-2H-pyrazol-3-yl]-benzo[c]isoxazole;
   3-(4-Fluoro-phenyl)-5-[2-(4-fluoro-phenyl)-2H-pyrazol-3-yl]-benzo[c]isoxazole;
   3-(3-Fluoro-phenyl)-5-[2-(4-fluoro-phenyl)-2H-pyrazol-3-yl]-benzo[c]isoxazole;
   5-[2-(4-Fluoro-phenyl)-2H-pyrazol-3-yl]-3-p-tolyl-benzo[c]isoxazole;
   3-(4-Chloro-phenyl)-5-(4-fluoro-phenyl)-2H-pyrazol-3-yl)-benzo[c]isoxazole;
   5-[2-(4-Fluoro-phenyl)-2H-pyrazol-3-yl]-3-(4-methoxy-phenyl)-benzo[c]isoxazole;
   3-(4-Fluoro-phenyl)-5-(2-p-tolyl-2H-pyrazol-3-yl)-benzo[c]isoxazole;
   3-(3-Fluoro-phenyl)-5-(2-p-tolyl-2H-pyrazol-3-yl)-benzo[c]isoxazole;
   3-p-Tolyl-5-(2-p-tolyl-2H-pyrazol-3-yl)-benzo[c]isoxazole;
   5-(2-p-Tolyl-2H-pyrazol-3-yl)-3-(4-trifluoromethyl-phenyl)-benzo[c]isoxazole;
   3-(4-Chloro-phenyl)-5-(2-p-tolyl-2H-pyrazol-3-yl)-benzo[c]isoxazole;
   3-(4-Methoxy-phenyl)-5-(2-p-tolyl-2H-pyrazol-3-yl)-benzo[c]isoxazole;
   3-(4-Fluoro-phenyl)-5-[2-(4-methoxy-phenyl)-2H-pyrazol-3-yl]-benzo[c]isoxazole;
   3-(3-Fluoro-phenyl)-5-[2-(4-methoxy-phenyl)-2H-pyrazol-3-yl]-benzo[c]isoxazole;
   5-[2-(4-Methoxy-phenyl)-2H-pyrazol-3-yl]-3-p-tolyl-benzo[c]isoxazole;
   3-(4-Chloro-phenyl)-5-[2-(4-methoxy-phenyl)-2H-pyrazol-3-yl]-benzo[c]isoxazole;
   3-(4-Methoxy-phenyl)-5-[2-(4-methoxy-phenyl)-2H-pyrazol-3-yl]-benzo[c]isoxazole;
   5-[2-(4-Chloro-phenyl)-2H-pyrazol-3-yl]-3-(4-fluoro-phenyl)-benzo[c]isoxazole;
   5-[2-(4-Chloro-phenyl)-2H-pyrazol-3-yl]-3-(3-fluoro-phenyl)-benzo[c]isoxazole;
   3-(4-Chloro-phenyl)-5-[2-(4-chloro-phenyl)-2H-pyrazol-3-yl]-benzo[c]isoxazole;
   5-[2-(2,4-Difluoro-phenyl)-2H-pyrazol-3-yl]-3-(4-fluoro-phenyl)-benzo[c]isoxazole;
   5-[2-(2,4-Difluoro-phenyl)-2H-pyrazol-3-yl]-3-(3-fluoro-phenyl)-benzo[c]isoxazole;
   5-[2-(2,4-Difluoro-phenyl)-2H-pyrazol-3-yl]-3-p-tolyl-benzo[c]isoxazole;
   5-[2-(2,4-Difluoro-phenyl)-2H-pyrazol-3-yl]-3-(4-trifluoromethyl-phenyl)-benzo[c]isoxazole;
   3-(4-Chloro-phenyl)-5-[2-(2,4-difluoro-phenyl)-2H-pyrazol-3-yl]-benzo[c]isoxazole;
   5-[2-(2,4-Difluoro-phenyl)-2H-pyrazol-3-yl]-3-(4-methoxy-phenyl)-benzo[c]isoxazole;
   3-Phenyl-5-(2-phenyl-2H-pyrazol-3-yl)-benzo[c]isoxazole;
   3-(3-Fluoro-4-methoxy-phenyl)-5-[2-(2-fluoro-phenyl)-2H-pyrazol-3-yl]-benzo[c]isoxazole;
   3-(3-Fluoro-4-methoxy-phenyl)-5-[2-(4-fluoro-phenyl)-2H-pyrazol-3-yl]-benzo[c]isoxazole;
   3-(3,4-Difluoro-phenyl)-5-(2-p-tolyl-2H-pyrazol-3-yl)-benzo[c]isoxazole;
   3-(3-Fluoro-4-methoxy-phenyl)-5-(2-p-tolyl-2H-pyrazol-3-yl)-benzo[c]isoxazole;
   5-[2-(2,4-Difluoro-phenyl)-2H-pyrazol-3-yl]-3-(3-fluoro-4-methoxy-phenyl)-benzo[c]isoxazole;
   5-[2-(2-Chloro-phenyl)-2H-pyrazol-3-yl]-3-(4-fluoro-phenyl)-benzo[c]isoxazole;
   3-(4-Chloro-phenyl)-5-[2-(2-chloro-phenyl)-2H-pyrazol-3-yl]-benzo[c]isoxazole;
   5-[2-(2-Chloro-phenyl)-2H-pyrazol-3-yl]-3-p-tolyl-benzo[c]isoxazole.

4. A compound of formula IB encompassed by compounds of formula I according to claim 1

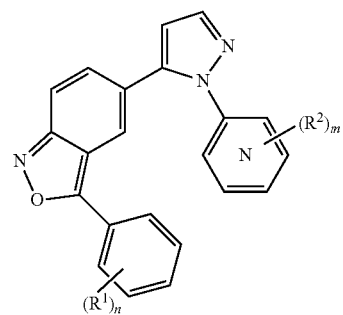

wherein

is a pyridine ring, wherein the N-atom may be in different positions,

R¹/R² is hydrogen, halogen, lower alkyl, CF₃ or lower alkoxy; and n,m are 1 or 2;

or a pharmaceutically acceptable acid addition salt, a racemic mixture or its corresponding enantiomer and/or optical isomers thereof.

5. A compound of formula I according to claim 1, which compound is 3-(4-Fluoro-phenyl)-5-(2-pyridin-2-yl-2H-pyrazol-3-yl)-benzo[c]isoxazole.

6. A compound of formula IC encompassed by compounds of formula I according to claim 1

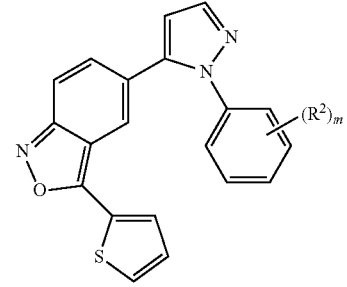

IC wherein

R² is hydrogen, halogen, lower alkyl, CF₃ or lower alkoxy; and m is 1 or 2;

or a pharmaceutically acceptable acid addition salt, a racemic mixture or its corresponding enantiomer and/or optical isomers thereof.

7. A compound of formula I according to claim 1, which compound is

5-[2-(4-Fluoro-phenyl)-2H-pyrazol-3-yl]-3-thiophen-2-yl-benzo[c]isoxazole.

8. A process for the manufacture of a compound of formula I as defined in claim 1, which process comprises reacting a compound of formula

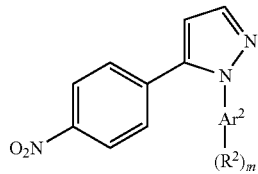

(3)

with a compound of formula $(R^1)_n$—Ar¹CH₂CN    (4)

to afford a compound of formula (I)

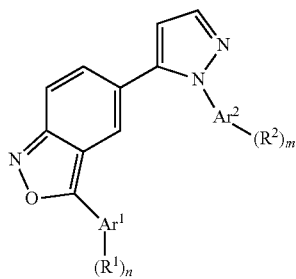

I wherein

Ar¹/Ar² are phenyl or a 5 or 6-membered heteroaryl,

R¹/R² is hydrogen, halogen, lower alkyl, CF₃ or lower alkoxy and n,m are 1 or 2;

and, if desired, converting the compounds obtained into pharmaceutically acceptable acid addition salts.

9. A pharmaceutical composition comprising a compound according to claim 1, and a pharmaceutical acceptable carrier and/or adjuvant.

\* \* \* \* \*